United States Patent [19]

Skuballa et al.

[11] Patent Number: 5,502,075
[45] Date of Patent: Mar. 26, 1996

[54] LEUKOTRIENE-$B_4$ DERIVATIVES, PROCESS FOR THEIR PRODUCTION AND THEIR USE AS PHARMACEUTICAL AGENTS

[75] Inventors: Werner Skuballa; Bernd Buchmann; Josef Heindl; Wolfgang Fröhlich; Roland Ekerdt; Claudia Giesen, all of Berlin, Germany

[73] Assignee: Schering Aktiengesellschaft, Berlin, Germany

[21] Appl. No.: 244,500

[22] PCT Filed: Nov. 19, 1992

[86] PCT No.: PCT/EP92/02653

§ 371 Date: May 27, 1994

§ 102(e) Date: May 27, 1994

[87] PCT Pub. No.: WO93/11105

PCT Pub. Date: Jun. 10, 1993

[30] Foreign Application Priority Data

Nov. 29, 1991 [DE] Germany .................. 41 39 868.8
Nov. 29, 1991 [DE] Germany .................. 41 39 869.6

[51] Int. Cl.⁶ .................... A61K 31/34; A61K 31/19
[52] U.S. Cl. .................... 514/461; 514/572; 549/295; 562/505; 562/508; 562/512; 560/190; 560/201

[58] Field of Search .................. 562/505, 508, 562/512; 549/295; 514/461, 572; 560/190, 201

[56] References Cited

FOREIGN PATENT DOCUMENTS 0399633 11/1990 European Pat. Off. .
WO92/16504 10/1992 WIPO .

*Primary Examiner*—C. Warren Ivy
*Assistant Examiner*—Amelia Owens
*Attorney, Agent, or Firm*—Millen, White Zelano, & Branigan

[57] ABSTRACT

Leukotriene-$B_4$ derivatives of formula I

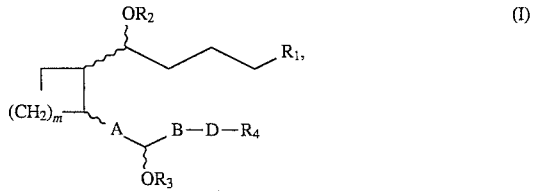

their salts with physiologically compatible bases and their cyclodextrin clathrates are described.

20 Claims, No Drawings

LEUKOTRIENE-B₄ DERIVATIVES, PROCESS FOR THEIR PRODUCTION AND THEIR USE AS PHARMACEUTICAL AGENTS

The invention relates to new leukotriene-B$_4$ derivatives, process for their production as well as their use as pharmaceutical agents. The new compounds are structural analogs of previously known leukotriene-B$_4$ antagonists, that contain a six-membered ring as a basic structural element (DE-A 39 17 597). Leukotriene B$_4$ (LTB$_4$) was discovered by B. Samuelsson et al. as a metabolite of arachidonic acid. In the biosynthesis, leukotriene A$_4$ is formed by the enzyme 5-lipoxygenase first as a central intermediate product, which then is converted by a specific hydrolase to the LTB$_4$.

KEY:

Arachidonsäure=arachidonic acid

Leukotrien A$_4$ (LTA$_4$)=leukotriene A$_4$ (LTA$_4$)

Glutathion-S-transferase=glutathione-S-transferase

Leukotrien B$_4$ (LTB$_4$)=leukotriene B$_4$ (LTB$_4$)

Leukotrien C$_4$ (LTC$_4$)=leukotriene C$_4$ (LTC$_4$)

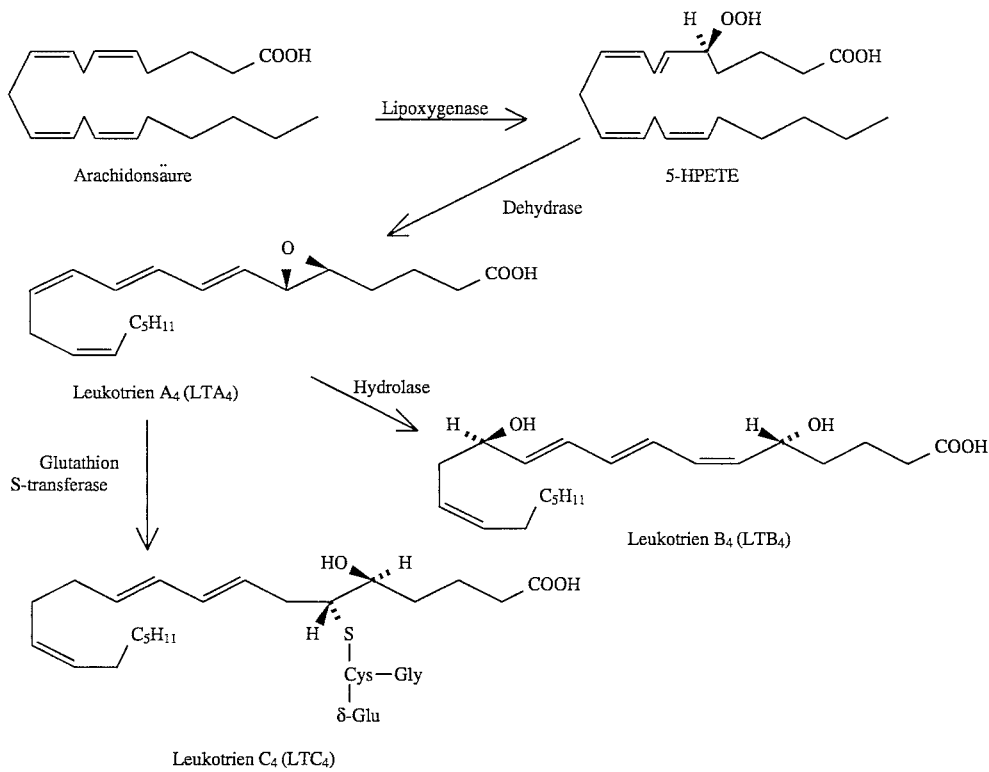

The nomenclature of the leukotrienes can be gathered from the following works:

a) B. Samuelsson et al., Prostaglandins 19, 645 (1980); 17, 785 (1979).

b) C. N. Serhan et al., Prastaglandins 34, 201 (1987).

The physiological and especially the pathophysiological importance of leukotriene B$_4$ is summarized in several more recent works: a) The Leukotrienes, Chemistry and Biology eds. L. W. Chakrin, D. M. Bailey, Academic Press 1984. b) J. W. Gillard et al., Drugs of the Future 12, 453 (1987). c) B. Samuelsson et al., Science 237, 1171 (1987). d) C. W. Parker, Drug Development Research 10, 277 (1987). It follows from the above that LTB$_4$ is an important inflammation mediator for inflammatory diseases, in which leukocytes invade the affected tissue.

It is known from the LTB$_4$ that it causes the adhesion of leukocytes on the blood vessel wall. LTB$_4$ is chemotactically effective, i.e., it triggers a directed migration of leukocytes in the direction of a gradient of increasing concentration. Further, because of its chemotactic activity, it indirectly changes the vascular permeability, and a synergism with prostaglandin E$_2$ is observed. LTB$_4$ obviously plays a decisive role in inflammatory, allergic and immunological processes.

Leukatrienes and especially LTB$_4$ are involved in skin diseases, which accompany inflammatory processes (increased vessel permeability and formation of edemas, cell infiltration), increased proliferation of skin cells and itching, such as, for example, in eczemas, erythemas, psoriasis, pruritus and acne. Pathologically increased leukotriene concentrations are involved either causally in the development of many dermatitides or there is a connection between the persistence of the dermatitides and the leukotrienes. Clearly increased leukotriene concentrations were measured, for example, in the skin of patients with psoriasis or atopic dermatitis. Further, leukotrienes and LTB$_4$ especially are involved in arthritis, chronic lung diseases (e.g., asthma), rhinitis and inflammatory intestinal diseases as well as reperfusion damages of various organs.

Antagonists against LTB$_4$ receptors or inhibitors of those enzymes which are involved in the synthesis of the LTB$_4$ should be effective as specific medications, especially against diseases which accompany inflammations and allergic reactions.

Besides therapeutic possibilities, which can be derived from counteracting of LTB$_4$ action with LTB$_4$ analogs, the usefulness and potential use of leukotriene-B$_4$ agonists for the treatment of fungus diseases of the skin was also able to be shown (H. Katayama, Prostaglandins 34, 797 (1988)).

The invention relates to leukotriene-$B_4$ derivatives of formula I

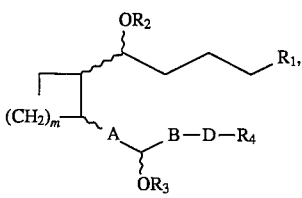

in which $R^1$ means $CH_2OH$, $CH_3$, $CF_3$, $COOR^5$ $CONR^6R^7$, or $R^1$ together with $R^2$ means a carbonyl group, $R^2$ and $R^3$, the same or different, represent H or an organic acid radical with 1–15 C atoms, $R^4$ symbolizes H, $C_1$–$C_{14}$ alkyl, optionally substituted once or several times, $C_3$–$C_{10}$ cycloalkyl, $C_6$–$C_{10}$ aryl radical optionally substituted, independent from one another, once or several times by halogen, phenyl, $C_1$–$C_4$ alkyl, $C_1$–$C_4$ alkoxy, fluoromethyl, chloromethyl, trifluoromethyl, carboxyl or hydroxy, or a 5–6 membered aromatic heterocyclic ring with at least 1 heteroatom, $R^5$ means hydrogen, $C_1$–$C_{10}$ alkyl, $C_3$–$C_{10}$ cycloalkyl, $C_6$–$C_{10}$ aryl radical optionally substituted by 1–3 halogen, phenyl, $C_1$–$C_4$ alkyl, $C_1$–$C_4$ alkoxy, fluoromethyl, chloromethyl, trifluoromethyl, carboxyl or hydroxy, $CH_2$—CO—($C_6$–$C_{10}$) aryl or a 5–6 membered ring with at least 1 heteroatom, A symbolizes a trans, trans—CH=CH—CH=CH, a —$CH_2CH_2$—CH=CH— or a tetramethylene group, B symbolizes a $C_1$–$C_{10}$ straight-chain or branched-chain alkylene group, which optionally can be substituted by fluorine or the group

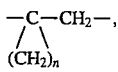

D can mean a direct bond, oxygen, sulfur, —C≡C—, —CH=$CR^8$ or together with

B can also mean a direct bond, $R^6$ and $R^7$ are the same or different and represent H or $C_1$–$C_4$ alkyl or $R^7$ represents H and $R^6$ represents $C_1$–$C_{15}$ alkanoyl or $C_1$–$C_{10}$ alkanesulfonyl, $R^8$ means H, $C_1$–$C_5$ alkyl, chlorine, bromine, m symbolizes the numbers 1 or 4 and n is 3–5 as well as, if $R^5$ means hydrogen, their salts with physiologically compatible bases and their cyclodextrin clathrates.

Groups $OR^2$ and $OR^3$ can be in α- or β-position. Formula I comprises both racemates and the possible pure diastereomers and enantiomers.

As alkyl groups $R^5$, straight-chain or branched-chain alkyl groups with 1–10 C atoms are suitable, such as, for example, methyl, ethyl, propyl, butyl, isobutyl, tert-butyl, pentyl, neopentyl, hexyl, heptyl, decyl. Alkyl groups $R^5$ can optionally be substituted once to several times by halogen atoms, alkoxy groups, optionally substituted aryl or aroyl groups with 6–10 C atoms (for possible substituents see under Aryl $R^5$), dialkylamino and trialkylammonium with 1–4 C atoms in the alkyl part, and the single substitution is to be preferred. As substituents, there can be mentioned, for example, fluorine, chlorine or bromine, phenyl, dimethylamino, diethylamino, methoxy, ethoxy. As preferred alkyl groups $R^5$, those with 1–4 C atoms are to be mentioned.

Cycloalkyl group $R^5$ can contain 3–10, preferably 5 and 6 carbon atoms in the ring. The rings can be substituted by alkyl groups with 1–4 carbon atoms. For example, there can be mentioned cyclopentyl, cyclohexyl, methylcyclohexyl.

As aryl groups $R^5$, both substituted and unsubstituted aryl groups with 6–10 C atoms are suitable, such as, for example, phenyl, 1-naphthyl and 2-naphthyl, each of which can be substituted by 1–3 halogen atoms (F, Cl, Br), a phenyl group, 1–3 alkyl groups each with 1–4 C atoms, a chloromethyl, fluoromethyl, trifluoromethyl, carboxyl, hydroxy or alkoxy group with 1–4 C atoms. Preferred substituents in 3- and 4-position on the phenyl ring are, for example, fluorine, chlorine, alkoxy or trifluoromethyl, however, hydroxy in 4-position.

As heterocyclic groups $R^5$, 5- and 6-membered aromatic heterocycles are suitable, which contain at least 1 heteroatom, preferably nitrogen, oxygen or sulfur. For example, there can be mentioned 2-furyl, 2-thienyl, 2-pyridyl, 3-pyridyl, 4-pyridyl, oxazolyl, thiazolyl, pyrimidinyl, pyridazinyl, pyrazinyl, 3-furyl, 3-thienyl, 2-tetrazolyl, i.a.

As acid radical $R^6$, physiologically compatible acid radicals are suitable. Preferred acids are organic carboxylic acids and sulfonic acids with 1–15 carbon atoms, which belong to the aliphatic, cycloaliphatic, aromatic, aromatic-aliphatic and heterocyclic series. These acids can be saturated, unsaturated and/or multibasic and/or substituted in the usual way. As examples for the substituents, $C_{1-4}$ alkyl, hydroxy, $C_{1-4}$ alkoxy, oxo or amino groups or halogen atoms (F, Cl, Br) can be mentioned. For example, the following carboxylic acids can be mentioned: formic acid, acetic acid, propionic acid, butyric acid, isobutyric acid, valeric acid, isovaleric acid, caproic acid, enanthic acid, caprylic acid, pelargonic acid, capric acid, undecanoic acid, lauric acid, tridecanoic acid, myristic acid, pentadecanoic acid, trimethylacetic acid, diethylacetic acid, tert-butylacetic acid, cyclopropylacetic acid, cyclopentylacetic acid, cyclohexylacetic acid, cyclopropanecarboxylic acid, cyclohexanecarboxylic acid, phenylacetic acid, phenoxyacetic acid, methoxyacetic acid, ethoxyacetic acid, mono-, di- and trichloroacetic acid, aminoacetic acid, diethylaminoacetic acid, piperidinoacetic acid, morpholinoacetic acid, lactic acid, succinic acid, adipic acid, benzoic acid, benzoic acids substituted with halogen (F, Cl, Br) or trifluoromethyl, hydroxy, $C_{1-4}$ alkoxy or carboxy groups, nicotinic acid, isonicotinic acid, furan-2-carboxylic acid, cyclopentylpropionic acid. As especially preferred acyl radicals and alkanesulfonyl radicals, those with up to 10 carbon atoms are suitable. As sulfonic acids, for example, methanesulfonic acid, ethanesulfonic acid, isopropanesulfonic acid, β-chloroethanesulfonic acid, butanesulfonic acid, cyclopentanesulfonic acid, cyclohexanesulfonic acid, benzenesulfonic acid, p-toluenesulfonic acid, p-chlorobenzenesulfonic acid, N,N-dimethylaminosulfonic acid, N,N-diethylaminosulfonic acid, N,N-bis-(β-chloroethyl)aminosulfonic acid, N,N-diisobutylaminosulfonic acid, N,N-dibutylaminosulfonic acid, pyrrolidino, piperidino, piperazino, N-methylpiperazino, and morpholinosulfonic acid are suitable.

As alkyl groups $R^4$, straight-chain and branched-chain, saturated and unsaturated alkyl radicals, preferably saturated, with 1–14, especially 1–10 C atoms, are suitable, which optionally can be substituted by optionally substituted phenyl (for substitution, see under Aryl $R^5$). For example, there can be mentioned methyl, ethyl, propyl, butyl, isobutyl, tert-butyl, pentyl, hexyl, heptyl, octyl, butenyl, isobutenyl, propenyl, pentenyl, benzyl, m- and p-chlorobenzyl groups. If alkyl groups $R^4$ are halogen-substituted, fluorine, chlorine and bromine are suitable as halogens.

As examples for halogen-substituted alkyl groups $R^4$, alkyls with terminal trifluoromethyl groups are suitable.

Cycloalkyl group $R^4$ can contain 3–10, preferably 3–6 carbon atoms in the ring. The rings can be substituted by alkyl groups with 1–4 carbon atoms. For example, there can be mentioned cyclopropyl, cyclobutyl, cyclopentyl, cyclohexyl, methylcyclohexyl.

As substituted or unsubstituted aryl groups $R^4$, for example, phenyl, 1-naphthyl and 2-naphthyl, which respectively can be substituted by 1–3 halogen atoms (Fl, Cl, Br), a phenyl group, 1–3 alkyl groups with respectively 1–4 C atoms, a chloromethyl, fluoromethyl, trifluoromethyl, carboxyl, $C_1$–$C_4$ alkoxy or hydroxy group are suitable. The substitution in 3- and 4-position on the phenyl ring, for example, by fluorine, chlorine, alkoxy or trifluoromethyl or in 4-position by hydroxy is preferred.

As heterocyclic aromatic groups $R^4$, 5- and 6-membered heterocycles are suitable which contain at least 1 heteroatom, preferably nitrogen, oxygen or sulfur. For example, there can be mentioned 2-furyl, 2-thienyl, 2-pyridyl, 3-pyridyl, 4-pyridyl, oxazolyl, thiazolyl, pyrimidinyl, pyridazinyl, pyrazinyl, 3-furyl, 3-thienyl, i.a.

As alkylene group B, straight-chain or branched-chain, saturated or unsaturated alkylene radicals, preferably saturated with 1–10, especially with 1–5 C atoms are suitable, which optionally can be substituted by fluorine atoms. For example, there can be mentioned: methylene, fluoromethylene, difluoromethylene, ethylene, 1,2-propylene, ethyl ethylene, trimethylene, tetramethylene, pentamethylene, 1,2-difluoroethylene, 1-fluoroethylene, 1-methyltetramethylene, 1-methyltrimethylene, 1-methylene-ethylene, 1-methylenetetramethylene.

Alkylene group B can further represent the group $$-\underset{\underset{(CH_2)_n}{\diagup\diagdown}}{C}-CH_2-,$$

in which n=3–5, preferably 4–5.

As acid radicals $R^2$ and $R^3$, physiologically compatible acid radicals are suitable. Preferred acids are organic carboxylic acids and sulfonic acids with 1–15 carbon atoms, which belong to the aliphatic, cyclo-aliphatic, aromatic, aromatic-aliphatic or heterocyclic series. These acids can be saturated, unsaturated and/or multibasic and/or substituted in the usual way. As examples for the substituents, $C_{1-4}$ alkyl, hydroxy, $C_{1-4}$ alkoxy, oxo or amino groups or halogen atoms (F, Cl, Br) can be mentioned.

For example, the following carboxylic acids can be mentioned: formic acid, acetic acid, propionic acid, butyric acid, isobutyric acid, valeric acid, isovaleric acid, caproic acid, enanthic acid, caprylic acid, pelargonic acid, capric acid, undecanoic acid, lauric acid, tridecanoic acid, myristic acid, pentadecanoic acid, trimethylacetic acid, diethylacetic acid, tert-butylacetic acid, cyclopentylacetic acid, cyclohexylacetic acid, cyclohexanecarboxylic acid, phenylacetic acid, phenoxyacetic acid, methoxyacetic acid, ethoxyacetic acid, mono-, di- and trichloroacetic acid, aminoacetic acid, diethylaminoacetic acid, piperidinoacetic acid, morpholinoacetic acid, lactic acid, succinic acid, adipic acid, benzoic acid, benzoic acids substituted with halogen (F, Cl, Br), trifluoromethyl, hydroxy, $C_{1-4}$ alkoxy or carboxy groups, nicotinic acid, isonicotinic acid, furan-2-carboxylic acid, cyclopentylpropionic acid. As especially preferred acid radicals $R^2$ and $R^3$, acyl radicals with up to 10 carbon atoms are suitable.

Alkyl radicals $R^6$ and $R^7$ are straight-chain or branched alkyl radicals, especially straight-chain, such as, for example, methyl, ethyl, propyl, butyl, pentyl, hexyl, especially preferably methyl.

$R^8$ as $C_{1-5}$ alkyl means straight-chain or branched-chain alkyl radicals such as were already mentioned for $R^4$ or $R^5$. Preferred alkyl radicals $R^8$ are methyl, ethyl, propyl and isopropyl.

Inorganic and organic bases are suitable for salt formation, as they are known to one skilled in the art for forming physiologically compatible salts. For example, there can be mentioned alkali hydroxides, such as sodium hydroxide and potassium hydroxide, alkaline-earth hydroxides, such as calcium hydroxide, ammonia, amines, such as ethanolamine, diethanolamine, triethanolamine, N-methylglucamine, morpholine, tris-(hydroxymethyl)-methylamine, etc.

To achieve the cyclodextrin clathrates, the compounds of formula I with α, β or γ-cyclodextrin are reacted. The β-cyclodextrin clathrates are preferred.

Preferred compounds of this invention are compounds of formula I, in which the radicals have the following meaning:

$R^1$ is $CH_2OH$, $COOR^5$ with $R^5$ meaning a hydrogen atom, an alkyl radical with 1–10 C atoms, a cycloalkyl radical with 5–6 C atoms, a phenyl radical optionally substituted by 1–2 chlorine, bromine, phenyl, $C_{1-4}$ alkyl, $C_{1-4}$ alkoxy, chloromethyl, fluoromethyl, trifluoromethyl, carboxy or hydroxy, A is a trans, trans-CH=CH—CH=CH— or tetramethylene group;

B is a straight-chain or branched-chain, saturated or unsaturated alkylene group with up to 10 C atoms, which optionally can be substituted by fluorine or the group $$-\underset{\underset{(CH_2)_n}{\diagup\diagdown}}{C}-CH_2-$$

with n=3–5;

D is a direct bond, oxygen, sulfur, a —C≡C— group or a —CH=CR$^8$ group with $R^8$ as hydrogen, $C_{1-5}$ alkyl, chlorine or bromine;

B and D together are a direct bond;

$R^2$ and $R^3$ are the same or different and mean hydrogen or an organic acid radical with 1–15 C atoms;

$R^1$ and $R^2$ together are a carbonyl group;

$R^4$ is a hydrogen atom, $C_{1-10}$ alkyl, cycloalkyl with 5–6 C atoms, a phenyl radical optionally substituted by 1–2 chlorine, bromine, phenyl, $C_{1-4}$ alkyl, $C_{1-4}$ alkoxy, chloromethyl, fluoromethyl, trifluoromethyl, carboxy or hydroxy and if $R^5$ means a hydrogen atom, their salts with physiologically compatible bases and their cyclodextrin clathrates.

Especially preferred compounds of this invention are compounds of formula I, in which the radicals have the following meaning:

$R^1$ is $CH_2OH$, $COOR^5$ with $R^5$ meaning a hydrogen atom, an alkyl radical with 1–4 C atoms;

$R^2$ and $R^3$ are the same or different and mean hydrogen or an organic acid radical with 1–6 C atoms;

$R^1$ and $R^2$ together are a carbonyl group;

$R^4$ is a hydrogen atom or $C_{1-10}$-alkyl

A is a trans, trans-CH=CH—CH=CH— or tetramethylene group;

B is a straight-chain or branched-chain alkylene group with up to 5 C atoms;

D is a direct bond or a —C≡C— group or a —CH=CR$^8$ group with $R^8$ as hydrogen or $C_{1-5}$ alkyl;

B and D together are a direct bond;

and if $R^5$ means a hydrogen atom, their salts with physiologically compatible bases and their cyclodextrin clathrates.

The invention further relates to a process for the production of compounds of formula I according to the invention, which is characterized in that an aldehyde of formula II

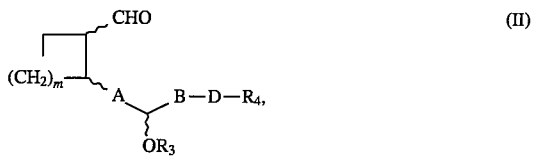

in which m, A, B, D, $R^3$ and $R^4$ have the above-indicated meanings, optionally after protection of free hydroxy groups with a magnesium-organic compound of formula III,

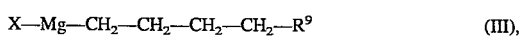

in which X represents chlorine, bromine or iodine and $R^9$ represents —$CH_3$, $CF_3$ or —$CH_2OR^{10}$, in which $R^{10}$ means an easily cleavable ether radical, is reacted and optionally then isomers are separated in any sequence, protected hydroxy groups are released and/or a free hydroxy group is esterified and/or the 1-hydroxy group is oxidized to carboxylic acid and/or double bonds are hydrogenated and/or an esterified carboxyl group ($R^1$=COOR$^5$) is saponified and/or reduced and/or a carboxyl group ($R^5$=H) is esterified and/or a free carboxy group ($R^5$=H) is converted to an amide ($R^1$=CONHR$^6$R$^7$) or a carboxyl group with a physiologically compatible base is converted to a salt.

As ether radicals $R^9$ in the compound of formula III, the radicals familiar to one skilled in the art are suitable. Easily cleavable ether radicals, such as, for example, dimethyl-tert-butylsilyl, trimethylsilyl, tribenzylsilyl, diphenyl-tert-butylsilyl, tetrahydropyranyl, tetrahydrofuranyl and α-ethoxyethyl, to name only a few, are preferable.

The reaction of the compound of formula II with an organometallic compound of formula III takes place in a way known in the art in an inert solvent or solvent mixture, such as, for example, dioxane, toluene, dimethoxyethane, or preferably diethyl ether or tetrahydrofuran. The reaction is performed at temperatures between −100° C. and 60° C., preferably at −78° C. to 0° C.

The production of the compound of formula III necessary for this reaction takes place by reaction of the corresponding hydroxy halide protected by an easily cleavable ether group and subsequent reaction with magnesium.

The reduction to the compounds of formula I with $R^1$ meaning a $CH_2OH$ group is performed with a reducing agent suitable for the reduction of esters or carboxylic acids, such as, for example, lithium aluminum hydride, diisobutyl aluminum hydride, etc. As solvent, diethyl ether, tetrahydrofuran, dimethoxyethane, toluene, etc., are suitable. The reduction is performed at temperatures of −30° C. up to boiling temperature of the solvent used, preferably 0° C. to 30° C.

The esterification of the alcohols of formula I ($R^2$=H and/or $R^3$=H) takes place in a way known in the art. For example, the esterification takes place in that an acid derivative, preferably an acid halide or acid anhydride, is reacted in the presence of a base, such as, for example, NaH, pyridine, triethylamine, tributylamine or 4-dimethylaminopryidine with an alcohol of formula I. The reaction can be performed without solvent or in an inert solvent, preferably acetone, acetonitrile, dimethylacetamide, DMSO at temperatures above or below room temperature, for example, between −80° C. to 100° C., preferably at room temperature.

The oxidation of the 1-hydroxy group is performed according to the methods known to one skilled in the art. As oxidizing agents, for example, there can be used: pyridinium dichromate (Tetrahedron Letters, 1979, 399), Jones reagent (J. Chem. Soc. 1953, 2555) or platinum/oxygen (Adv. in Carbohydrate Chem. 17, 169 (1962)) or Collins oxidation (Tetrahedron Letters 1968, 3363), and subsequent Jones oxidation. The oxidation with pyridinium dichromate is performed at temperatures of 0° C. to 100° C. preferably 20° C. to 40° C. in a solvent inert toward the oxidizing agent, for example, dimethylformamide.

The oxidation with Jones reagent is performed at temperatures of −40° C. to +40° C., preferably 0° C. to 30° C. in acetone as solvent.

The oxidation with platinum/oxygen is performed at temperatures of 0° C. to 60° C., preferably 20° C. to 40° C. in a solvent inert toward the oxidizing agent, such as, e.g., ethyl acetate.

The saponification of the esters of formula I is performed according to the methods known to one skilled in the art, such as, for example, with basic catalysts. The compounds of formula I can be separated by the usual separating methods into the optical isomers.

The release of the functionally modified hydroxy groups takes place according to known methods. For example, the cleavage of hydroxy protecting groups, such as, for example, the tetrahydropyranyl radical, is performed in an aqueous solution of an organic acid, such as, e.g., oxalic acid, acetic acid, propionic acid, i.a., or in an aqueous solution of an inorganic acid, such as, e.g., hydrochloric acid. To improve the solubility, a water-miscible, inert organic solvent is suitably added. Suitable organic solvents are, e.g., alcohols, such as methanol and ethanol, and ethers, such as dimethoxyethane, dioxane and tetrahydrofuran. Tetrahydrofuran is preferably used. The cleavage is performed preferably at temperatures between 20° C. and 80° C. The cleavage of the silyl ether protecting groups takes place, for example, with tetrabutylammonium fluoride or with potassium fluoride in the presence of a crown ether. As solvent, for example, tetrahydrofuran, diethyl ether, dioxane, methylene chloride, etc., are suitable. The cleavage is performed preferably at temperatures between 0° C. and 80° C.

The saponification of the acyl groups takes place, for example, with alkali or alkaline-earth carbonates or hydroxides in an alcohol or in the aqueous solution of an alcohol. As an alcohol, aliphatic alcohols are suitable, such as, e.g., methanol, ethanol, butanol, etc., preferably methanol. As alkali carbonates and hydroxides, potassium salts and sodium salts can be mentioned. The potassium salts are preferred.

As alkaline-earth carbonates and hydroxides, for example, calcium carbonate, calcium hydroxide and barium carbonate are suitable. The reaction takes place at −10° C. to +70° C., preferably at +25° C.

The introduction of ester group —COOR$^5$ for $R^1$ in which $R^5$ represents an alkyl group with 1–10 C atoms, takes place according to the methods known to one skilled in the art. The 1-carboxy compounds are reacted, for example, with diazohydrocarbons in a way known in the art. The esterification with diazohydrocarbons takes place, e.g., in that a solution of the diazohydrocarbon in an inert solvent, preferably in diethyl ether, is mixed with the 1-carboxy compound in the same or in another inert solvent, such as, e.g., methylene chloride. After completion of the reaction in 1 to 30 minutes, the solvent is removed and the ester is purified in the usual way. Diazoalkanes are either known or can be produced according to known methods [Org. Reactions Vol. 8, pages 389–394 (1954)].

The introduction of ester group —COOR⁵ for R¹, in which R⁵ represents a substituted or unsubstituted aryl group, takes place according to the methods known to one skilled in the art. For example, the 1-carboxy compounds with the corresponding arylhydroxy compounds are reacted in an inert solvent with dicyclohexylcarbodiimide in the presence of a suitable base, for example, pyridine, DMAP, triethylamine. As solvent, methylene chloride, ethylene chloride, chloroform, ethyl acetate, tetrahydrofuran, preferably chloroform, are suitable. The reaction is performed at temperatures between −30° C. and +50° C., preferably at 10° C.

If C═C double bonds contained in the primary product are to be reduced, the hydrogenation takes place according to methods known in the art.

The hydrogenation of the $\Delta^{8,10}$ diene system is performed in a way known in the art at low temperatures, preferably at about −20° C. to +30° C. in a hydrogen atmosphere in the presence of a noble metal catalyst. As catalyst, for example, 10% palladium on carbon is suitable.

The leukotriene-$B_4$ derivatives of formula I with R⁵ meaning a hydrogen atom can be converted to a salt with suitable amounts of the corresponding inorganic bases with neutralization. For example, during dissolving of the corresponding acids in water, which contains the stoichiometric amount of the base, the solid inorganic salt is obtained after evaporation of the water or after addition of a water-miscible solvent, e.g., alcohol or acetone.

For the production of an amine salt, the $LTB_4$ acid, e.g., is dissolved in a suitable solvent, for example, ethanol, acetone, diethyl ether, acetonitrile or benzene and at least the stoichiometric amount of the amine is added to this solution. In this way, the salt usually accumulates in solid form or is isolated after evaporation of the solvent in the usual way.

The introduction of amide group —$CONHR_6$ with $R_6$ meaning alkanoyl takes place according to the methods known to one skilled in the art. The carboxylic acids of formula I ($R_5$=H) are first converted to the mixed anhydride in the presence of a tertiary amine, such as, for example, triethylamine, with chloroformic acid isobutyl ester. The reaction of the mixed anhydride with the alkali salt of the corresponding amide or with ammonia ($R_6$=H) takes place in an inert solvent or solvent mixture, such as, for example, tetrahydrofuran, dimethoxyethane, dimethylformamide, hexamethylphosphoric acid triamide, at temperatures between −30° C. and +60° C., preferably at 0° C. to 30° C.

Another possibility for the introduction of amide group —$CONHR_6$ consists in the reaction of a 1-carboxylic acid of formula I ($R_5$=H), in which free hydroxy groups are optionally intermediately protected, with compounds of formula IV,

O═C═N-R₆     (IV), in which $R_6$ has the above-indicated meaning.

The reaction of the compound of formula I ($R_5$=H) with an isocyanate of formula IV takes place optionally by adding a tertiary amine, such as, e.g., triethylamine or pyridine. The reaction can be performed without solvent or in an inert solvent, preferably acetonitrile, tetrahydrofuran, acetone, dimethylacetamide, methylene chloride, diethyl ether, toluene, at temperatures between −80° C. to 100° C., preferably at 0° C. to 30° C.

For production of the other amides, for example, the desired acid anhydrides can be reacted with ammonia or the corresponding amines.

If the initial product contains OH groups in the leukotriene-$B_4$ radical, these OH groups are also reacted. If finally end products are desired which contain free hydroxyl groups, a start is suitably made from initial products in which the latter are intermediately protected by preferably easily cleavable ether or acyl radicals.

The separation of enantiomers and/or diastereomers takes place according to the methods known to one skilled in the art, for example, high-pressure liquid chromatography on optically active vehicles.

The compounds of formula II with m meaning 1 being used as initial material can be produced, for example, by cis- or trans-bis-1,2-hydroxymethyl-cyclobutane (obtainable by reduction from cis- or trans-cyclobutane-1,2-dicarboxylic acid, see, e.g., analogously to A. Padwa et al., J. Org. Chem. 54, 817 (1989); O. Caamaus et al., Eur. J. Med. Chem. 22, 311 (1987) J. B. Jones et al., J. A. Chem. Soc., 104, 4659 (1982)) being converted in a way known in the art to the monosilylether of formula Va

in which $R^{11}$, $R^{12}$ and $R^{15}$ are the same or different and mean $C_{1-4}$ alkyl or phenyl.

By oxidation, e.g., with Collins reagent or by the Swern process (Tetrahedron Letters 34, 1651 (1978)), there is obtained the aldehyde of formula VIa

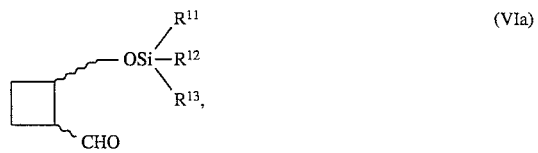

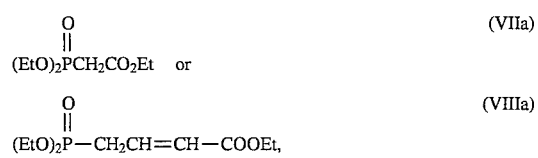

which is converted in a Wittig-Horner olefination with the phosphonate of formula VIIa and a base and optionally subsequent hydrogenation as well as subsequent reduction of the ester group, oxidation of the primary alcohol, repeated Wittig-Horner olefination with the phosphonate of formula VIIa and optionally subsequent hydrogenation to the ester of formula IXa or in a Wittig-Horner reaction of the aldehyde of formula VI with a phosphate of formula VIIIa, in which A

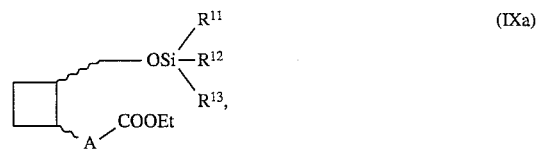

has the above-indicated meaning. As bases, for example, potassium-tert-butylate, diazabicyclononane, diazabicycloundecane, or sodium hydride are suitable. Reduction of the ester group, for example with diisobutyl aluminum hydride and subsequent oxidation of the obtained primary alcohol, e.g., with manganese dioxide or Collins reagent results in the aldehyde of formula Xa

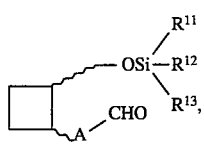

The organometallic reaction of the aldehyde of formula X with a Grignard reagent of formula XIa, $$X-Mg-B-D-R_4 \quad (XIa),$$

in which B, D and $R^4$ exhibit the above-indicated meanings and X means chlorine, bromine or iodine, results, after protection of the hydroxy group (for example, by acylation) and optionally diastereomer separation in the compounds of formula XIIa

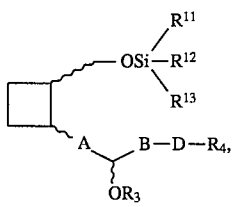

The production of the compound of formula XIa necessary for the organometallic reaction takes place by reaction of the corresponding terminal halide with magnesium. By reaction of silylether XIIa with tetrabutylammonium fluoride and optionally diastereomer separation, the alcohol of formula XIIIa is obtained.

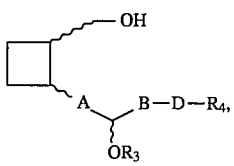

The oxidation of the primary alcohol group in XIII, e.g., Collins reagent or pyridinium dichromate, results in the aldehyde of formula II.

The compounds of formula XII, in which B means a $CH_2$ group and D means a $CH=CR^8$ group, can be achieved, for example, by an organometallic reaction of a propargyl halide and subsequent alkylation with a corresponding alkyl halide and optionally subsequent Lindlar hydrogenation.

An alternative design of the lower chain starts from the aldehyde of formula XIVa, which resulted from the Wittig-Horner reaction of aldehyde VI and subsequent reduction and oxidation.

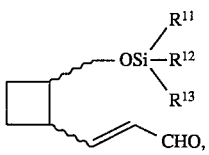

Wittig-Horner olefination of aldehyde XIII with a phosphonate of formula XVa

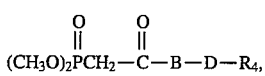

and reduction of the resulting ketone then resulted in the alcohol of formula XIIIa that can be separated in the diastereomers.

The separation of enantiomers and/or diastereomers takes place according to the methods known to one skilled in the art, for example, high-pressure liquid chromatography on optically active vehicles.

The compounds of formula II with m meaning 4 being used as initial material can be produced, for example, by an ester of cis- or trans-bis-1,2-dicarboxylic acid-cycloheptane (known by example from G. Sicher et al., Collection Czechoslov. Chem. Commun. 24, 262 (1961)) being converted in a way known in the art by reduction to the diol of formula Vb

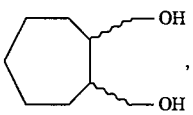

The diol of formula Vb can then be subsequently converted according to known methods into the monosilyl ether of formula VIb

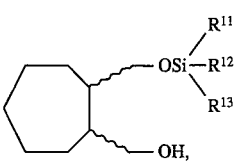

in which $R^{11}$, $R^{12}$ and $R^{13}$ are the same or different and mean $C_1$–$C_4$-alkyl or phenyl.

By oxidation, e.g., with Collins reagent or by the Swern process (Tetrahedron Letters 34, 1651 (1978)), there is obtained the aldehyde of formula VIIb

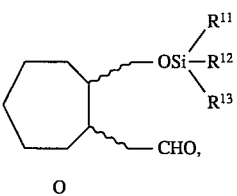

$$(EtO)_2PCH_2CO_2Et \quad (VIIIb)$$

or $$(EtO)_2P-CH_2CH=CH-COOEt, \quad (IXb)$$

which is converted in a Wittig-Horner olefination with the phosphonate of formula VIII and a base and optionally subsequent hydrogenation as well as subsequent reduction of the ester group, oxidation of the primary alcohol, again Wittig-Horner olefination with the phosphonate of formula VIII and optionally subsequent hydrogenation in the ester of formula Xb

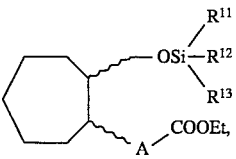

or in a Wittig-Horner reaction of the aldehyde of formula VIIb with a phosphonate of formula IXb, (in this way a cis/trans-isomerization in the ring system can partially take place, and the isomers are separable in later stages), in which A has the above-indicated meaning. As bases, for example, potassium-tert-butylate, diazabicycloundecane, diazabicyclononane or sodium hydride are suitable. Reduction of the ester group, for example with diisobutyl aluminum hydride and subsequent oxidation of the obtained primary alcohol, e.g., with manganese dioxide or Collins reagent results in the aldehyde of formula XIb

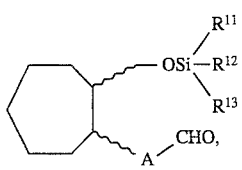

The organometallic reaction of the aldehyde of formula XI with a Grignard reagent of formula XIIb, $$X-Mg-B-D-R_4 \quad (XIIb),$$

in which B, D and $R^4$ exhibit the above-indicated meanings and X means chlorine, bromine or iodine, results, after protection of the hydroxy group and optionally diastereomer separation (for example, by acylation) in the compounds of formula XIIIb

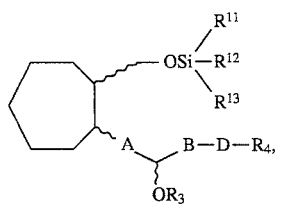

The production of the compound of formula XIIb necessary for the organometallic reaction takes place by reaction of the corresponding terminal halide with magnesium. By reaction of silylether XIIIb with tetrabutylammonium fluoride and optionally diastereomer separation, the alcohol of formula XIVb is obtained.

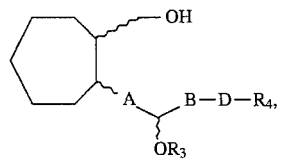

The oxidation of the primary alcohol group in XIVb, e.g., Collins reagent or pyridinium dichromate, results in the aldehyde of formula II.

The compounds of formula XIII, in which B means a $CH_2$ group and D means a $CH=CR^8$ group, can be achieved, for example, by an organometallic reaction of a propargyl halide and subsequent alkylation with a corresponding alkyl halide and optionally subsequent Lindlar hydrogenation.

An alternative design of the lower chain starts from the aldehyde of formula XV, which resulted from the Wittig-Horner reaction of aldehyde VIIb and subsequent reduction and oxidation.

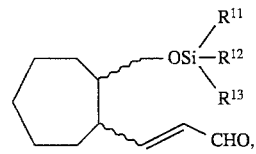

Wittig-Horner olefination of aldehyde XV with a phosphonate of formula XVIb

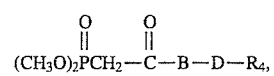

and reduction of the resulting ketone then resulted in the alcohol of formula XIIIb that can be separated in the diastereomers.

The incorporation of the chemically and metabolically labile cis-$\Delta^{6,7}$ double bond of the $LTB_4$ in a cis- or trans-1,2-substituted cycloheptyl ring results in a stabilization, and especially by further derivatizing of the functional groups, $LTB_4$ derivatives are obtained which can act as $LTB_4$ antagonists.

The compounds of formula I act in an antiinflammatory and antiallergic manner. In addition, they have antimycotic properties. Consequently, the new leukotriene-$B_4$ derivatives of formula I represent valuable pharmaceutical active ingredients. The compounds of formula I are especially suitable for topical administration, since they exhibit a dissociation between desired topical effectiveness and undesirable systemic side effects.

The new leukotriene-$B_4$ derivatives of formula I are suitable in combination with the auxiliary agents and vehicles usual in galenic pharmaceutics for topical treatment of contact dermatitis, eczemas of the most varied types, neurodermatoses, erythrodermia, pruritus vulvae et ani, rosacea, lupus erythematosus cutaneus, psoriasis, lichen ruber planus et verrucosis and similar skin diseases.

The production of the pharmaceutical agent specialties takes place in the usual way by the active ingredients being converted with suitable additives to the desired form of administration, such as, for example: solutions, lotions, ointments, creams or plasters.

In the thus formulated pharmaceutical agents, the active ingredient concentration depends on the form of administration. In lotions and ointments, an active ingredient concentration of 0.0001% to 1% is preferably used.

Further, the new compounds optionally in combination with the usual auxiliary agents and vehicles are also well-suited for the production of inhalants, which can be used to treat allergic diseases of the respiratory system, such as, for example, bronchial asthma or rhinitis.

Further, the new leukotriene-$B_4$ derivatives are also suitable in the form of capsules, tablets or coated tablets, which preferably contain 0.1 to 100 mg of active ingredient or are administered orally or in the form of suspensions, which preferably contain 1–200 mg of active ingredient per dosage unit, and are also administered rectally to treat allergic diseases of the intestinal tract, such as colitis ulcerosa and colitis granulomatosa.

The new leukotriene-$B_4$ derivatives can also be used in combination, such as, e.g., with lipoxygenase inhibitors, cyclooxygenase inhibitors, prostacyclin agonists, thromboxane antagonists, leukotriene-$D_4$ antagonists, leukotriene-$E_4$ antagonists, leukotriene-$F_4$ antagonists, phosphodiesterase inhibitors, calcium antagonists or PAF antagonists.

The following embodiments are used to explain the process according to the invention in more detail. In the examples, diastereoisomers in 5-position not characterized in more detail were characterized as polar or nonpolar (e.g., diastereomer nonpolar (5)).

EXAMPLE 1

(+/-)-(5RS)-5-Acetoxy-5-[cis-(2RS)-2-((1E,3E)-(5RS)-5-acetoxy-1,3-tridecadienyl)-(1RS)-cyclobutyl]-pentanoic acid diastereomer polar (5)

A solution of 8.9 g of 4-chloro-1-(tert.-butyldimethylsilyloxy)-butane in 8 ml of tetrahydrofuran is instilled in 1.92 g of magnesium at 25° C. under argon, a crystal of iodine is added, it is heated for 10 minutes to 70° C. stirred for 30 minutes at 25° C. and diluted with 25 ml of tetrahydrofuran.

A solution of 4.8 g of cis-(1RS)-1-formyl-(2RS)-2[(1E, 3E)-(5RS)-5-acetoxy-1,3-tridecadienyl]-cyclobutane in 40 ml of tetrahydrofuran is instilled in 30 ml of this magnesium-organic solution at −70° C. under argon and stirred for 0.5 hours at −70° C. It is mixed with 50 ml of saturated ammonium chloride solution, extracted three times with diethylether, the organic phase is shaken with semiconcentrated aqueous sodium chloride solution, dried on anhydrous sodium sulfate and concentrated by evaporation in a vacuum. The residue is chromatographed on silica gel. With hexane/ethyl acetate (8+2), 3 diastereomeric 5-(tert.-butyldimethylsilyloxy)- 1-cis{2-[((1E,3E)-(5RS)-5-acetoxy-1,3 -tridecadienyl]-cyclobutyl}-pentan-1-ol diastereomers are obtained in the sequence of increasing polarities.

0.7 g diastereomer nonpolar(5), A 0.6 g diastereomer nonpolar(5), B 3.6 g diastereomer polar(5)

IR(CNCl$_3$): 3580, 2930, 2860, 1728, 1252, 995, 838 cm$^{-1}$.

For acetylation, 4.5 ml of acetic anhydride is added to a solution of 3.5 g of the above-described alcohol indicated as (polar(5)-diastereomer) in 9 ml of pyridine and stirred for 23 hours at room temperature. Then it is concentrated by evaporation in a vacuum while adding toluene and the residue is chromatographed on silica gel. With hexane/diethyl ether (8+2), 3.7 g of the corresponding acetate is obtained as colorless oil.

IR: 2930, 2862, 1728, 1610, 1375, 1254, 993, 839 cm$^{-1}$.

For silyether cleavage, 3.67 g of the above-produced acetate in 130 ml of tetrahydrofuran is stirred with 3.67 g of tetrabutylammonium fluoride for 30 minutes at 0° C. and for 3 hours at 24° C. under argon. Then, it is diluted with diethylether, washed three times with water, dried on anhydrous magnesium sulfate and concentrated by evaporation in a vacuum. The residue is chromatographed with diethylether on silica gel. In this way, 2.84 mg of (±)-(5RS)-5-acetoxy-5-[cis-(2RS)-2-((1E,3E)-(5RS)-5 -acetoxy-1,3-tridecadienyl)-(1RS)-cyclobutyl]-pentan-1-ol is obtained as colorless oil.

IR: 3600 (broad), 2930, 2860, 1726, 1610, 1370, 1250, 990 cm$^{-1}$.

For oxidation of the 1-hydroxy group, 16.4 g of Collins reagent (bis-pyridine-chromium(VI)-oxide complex; Tetrahedron Letters 1968, 3363) is added to 2.76 g of the above-produced alcohol in 150 ml of dichloromethane at 0° C. and stirred for 20 minutes at 0° C. Then, it is diluted with a mixture of hexane/diethyl ether (1+1), Celite is added, filtered, washed with hexane/diethyl ether (1+1) and concentrated by evaporation in a vacuum. The thus obtained 1-aldehyde is immediately further processed without further purification.

5.3 ml of Jones reagent (chromium(VI)-oxide in H$_2$SO$_4$) (J. Chem. Soc. 1953, 2555) is instilled in a solution of 2.47 g of the thus produced aldehyde in 50 ml of acetone with stirring at −25° C. and stirred for 15 minutes at −25° C. under argon. Then, 3 ml of 2-propanol is added, stirred for 5 minutes, diluted with 250 ml of diethyl ether, shaken twice with semiconcentrated aqueous sodium chloride solution, dried on anhydrous magnesium sulfate and concentrated by evaporation in a vacuum. The residue is chromatographed on silica gel. With hexane/diethyl ether (1+1), 1.96 g of the title compound is obtained as colorless oil.

IR: 3520 (broad), 2930, 2860, 1728, 1375, 1250, 990, 948 cm$^{-1}$.

The initial material for the above title compound is produced as follows:

1a) 3-[cis-1-(tert.-Butyl-dimethylsilyloxymethyl)-cyclobut-2-yl]-(2E)-propenoic acid ethyl ester 46 ml of a 1.2 molar solution of diisobutylaluminum hydride in toluene is instilled in a solution of 2.8 g of 2 -hydroxymethyl-cyclobutanecarboxylic acid lactone (C. C. Schroff et al., J. Org. Chem. 36, 3356 (1971)) in 70 ml of toluene at 0° C. under argon and stirred for 50 minutes at 0° C. Then, 20 ml of 2-propanol and 23 ml of water are instilled, stirred for 2 hours at 22° C. filtered washed with dichloromethane and concentrated by evaporation in a vacuum. The residue is purified by chromatography on silica gel. With ethyl acetate/hexane (4+1), 2.1 g of cis-1,2-dihydroxymethyl-cyclopentane is obtained as colorless liquid.

IR: 3600, 3400, 2960, 1060 cm$^{-1}$.

A solution of 7.8 g of the above-produced diol in 12 ml of tetrahydrofuran is instilled in a suspension of 2.93 g of sodium hydride (as a 55% suspension in mineral oil) in 130 ml of tetrahydrofuran at 22° C. and stirred for 45 minutes at 22° C. Then, 10 g of tert.-butyldimethylsilyl chloride is added, stirred for 45 minutes at 22° C. and then diluted with about 0.8 liters of diethyl ether. The ether extract is washed with 10% aqueous potassium carbonate solution, shaken three times with water, dried with anhydrous sodium sulfate and concentrated by evaporation in a vacuum. The residue is chromatographed on silica gel. With hexane/diethyl ether (95+5), 16.9 g of cis-1 -tert.-butyl-dimethylsilyloxymethyl)-2-hydroxymethyl-cyclobutane is obtained as colorless liquid.

IR: 3420 (broad), 2960, 2863, 1260, 840 cm$^{-1}$.

70 g of Collins reagent (chromic acid-pyridine complex) is added to a solution of 9 g of the above-described monosilylether in 450 ml of dichloromethane at 0° C. and stirred for 30 minutes at 0° C. Then, it is diluted with a mixture of hexane/diethyl ether (3+2), Celite is added, filtered and concentrated by evaporation in a vacuum. 8.7 g of the aldehyde is obtained which is used without further purification.

IR: 2958, 2930, 2860, 2740, 1713, 840 cm$^{-1}$.

For the Wittig olefination, 12 g of phosphonoacetic acid triethyl ester and 7.2 g of diazabicycloundecene (DBU) are added at 24° C. to a stirred suspension of 2.3 g of lithium chloride in 150 ml of acetonitrile and stirred for 15 minutes. Then, a solution of 8.7 g of the above-described aldehyde in 24 ml of acetonitrile is instilled, stirred for 2.5 hours at 24° C. and then diluted with diethyl ether. It is shaken in succession with water, 10% aqueous sulfuric acid and water, dried with anhydrous sodium sulfate and concentrated by evaporation in a vacuum. The residue is chromatographed with hexane/diethyl ether (95+5) on silica gel. In this way, 9.0 g of the title compound is obtained as colorless oil.

IR: 2950, 2860, 1710, 1650, 1260, 993, 840 cm$^{-1}$.

1b) 5-[cis-1-(tert.-butyl-dimethylsilyloxymethyl)-cyclobut-2-yl]-(2E,4E)pentadienoic acid ethyl ester 129 ml of a 1.2 molar solution of diisobutylaluminum hydride in toluene is instilled in a solution of 21 g of the α,β-unsaturated ester, produced according to example 1a, in 250 ml of toluene at −70° C. under argon and stirred for 30 minutes at −70° C. Then, 30 ml of 2-propanol and then 60 ml of water are instilled, stirred for 2 hours at 22° C. filtered washed with dichloromethane and concentrated by evaporation in a vacuum. 18.1 g of 3-[cis-1-(tert.butyldimethylsilyloxy-methyl)-cyclo-but-2-yl]-(2E)-2-propen-1-ol is obtained, which is used without further purification.

IR: 3600, 3400, 2058, 840 cm$^{-1}$.

A solution of 18 g of the above-produced alcohol in 400 ml of toluene is mixed with 61 g of manganese dioxide and stirred for 5 hours at 24° C. Then, it is filtered, concentrated by evaporation and chromatographed on silica gel. With hexane/diethyl ether (92+8), 17.6 g of the aldehyde is eluted as colorless oil.

IR: 2950, 2860, 2740, 1680, 1633, 1470, 975, 840 cm$^{-1}$.

For Wittig olefination, 19.4 g of phosphonoacetic acid triethyl ester and 11.7 g of diazabicycloundecene are added at 24° C. to a stirred suspension of 3.66 g of lithium chloride in 255 ml of acetonitrile and stirred for 15 minutes. Then, a solution of 15.7 g of the above-described α,β-unsaturated aldehyde in 40 ml of acetonitrile is instilled, stirred for 4 hours at 24° C. and then diluted with diethyl ether. It is shaken in succession with water, 10% aqueous citric acid solution and water, dried with anhydrous sodium sulfate and concentrated by evaporation in a vacuum. The residue is chromatographed with hexane/diethyl ether (9+1) on silica gel. In this way, 11.9 g of the title compound is obtained as colorless oil.

IR: 2958, 2860, 1703, 1638, 1615, 1255, 1003, 970, 837 $cm^{-1}$.

1c) 5-[cis-1-(tert.-Butyl-dimethylsilyloxy-methyl)-cyclobut-2-yl]-(2E,4E)-pentadien-1-ol 76 ml of a 1.2 molar solution of diisobutylaluminum hydride in toluene is instilled in a solution of 12 g of the ester, produced according to example 1b, in 200 ml of toluene at −70° C. under argon and stirred for 30 minutes at −70° C. Then, 30 ml of 2-propanol and then 40 ml of water are instilled, stirred for 3 hours at 23° C., filtered, washed with dichloromethane and concentrated by evaporation in a vacuum. The residue is purified by chromatography on silica gel. With hexane/diethyl ether (8+2), 7.5 g of the alcohol is obtained as colorless oil.

IR: 3620, 3460, 838 $cm^{-1}$.

A solution of 7.3 g of the above-produced alcohol in 150 ml of toluene is mixed with 23.3 g of manganese dioxide and stirred for 6 hours at 24° C. Then, it is filtered, concentrated by evaporation and chromatographed on silica gel. With hexane/diethyl ether (9+1), 5.4 g of the title compound is obtained as colorless oil.

IR: 2955, 2858, 2740, 1683, 1634, 991, 842 $cm^{-1}$.

1d) (5RS)-5-Acetoxy-1-[cis-1-(tert.-butyldimethylsilyloxymethyl)-cyclobut- 2-yl]-(1E,3E)-tridecadiene A solution of 8.9 g of octyl bromide in 10 ml of diethyl ether is instilled in 1.12 g of magnesium in 4 ml of diethyl ether with heating and stirred for 30 minutes at 25° C.

A solution of 5.1 g of the aldehyde, produced according to example 1c, in 60 ml of diethyl ether is instilled in 9.6 ml (=20.0 mmol) of this Grignard solution at −20° C. under argon and stirred for 45 minutes at −20° C. It is mixed with saturated aqueous ammonium chloride solution, extracted three times with diethyl ether, the organic phase is shaken with semiconcentrated aqueous sodium chloride solution, dried on anhydrous sodium sulfate and concentrated by evaporation in a vacuum. The residue is chromatographed on silica gel. With hexane/ethyl acetate, 7.0 g of the corresponding alcohol is obtained as diastereomeric mixture.

For acetylation, 10 ml of acetic anhydride is added to a solution of 6.96 g of the above-produced diastereomeric alcohol mixture in 20 ml of pyridine and stirred for 24 hours at room temperature. Then, it is concentrated by evaporation in a vacuum while adding toluene and the residue is chromatographed on silica gel. With hexane/diethyl ether (95+5), 7.5 g of the title compound (nonpolar diastereomer) is obtained as colorless oil.

IR: 2938, 2860, 1725, 1655, 1250, 990, 838 $cm^{-1}$.

1e) cis-(1RS)-1-Formyl-(2RS)-2-[(1E,3E)-(5RS)-5-acetoxy-1,3-tridecadienyl]-cyclobutane 10.83 g of tetrabutylammonium fluoride is added to a solution of 7.5 g of the acetate produced according to example 1d, in 170 ml of tetrahydrofuran at 0° C. stirred for 15 minutes at 0° C. and for 5.5 hours at 24° C. Then, it is diluted with 1 liter of diethyl ether and washed three times with semiconcentrated aqueous sodium chloride solution. It is dried on anhydrous magnesium sulfate, concentrated by evaporation in a vacuum and the residue is chromatographed on silica gel. With hexane/diethyl ether (7+3), 5.2 g of (5RS)-1-(cis-hydroxymethylcyclobut-2-yl)-(1E,3E)-tridecadiene is eluted as colorless oil.

IR: 3610, 3450, 2930, 2860, 1726, 1250, 992 $cm^{-1}$.

32 g of Collins reagent (chromic acid-pyridine complex) is added to a solution of 5.0 g of the above-produced alcohol in 140 ml of dichloromethane at 0° C. and stirred for 20 minutes at 0° C. Then, it is diluted with a mixture of hexane/diethyl ether (1+1), Celite is added, filtered and concentrated by evaporation in a vacuum. The thus obtained aldehyde was used without further purification. (Crude yield 4.8 g).

IR: 2930, 2860, 2730, 1721, 1250, 990 $cm^{-1}$.

EXAMPLE 2

(±)-(5RS)-5-Hydroxy-5-[cis-(2RS)-2-((1E,3E)-(5RS)-5-hydroxy-1,3-tridecadienyl)-(1RS)-cyclobutyl]-pentanoic acid Diastereomer polar (5)

4.5 ml of a 0.5 molar aqueous lithium hydroxide solution is added to a solution of 200 mg of the diacetate (diastereomer polar (5)), produced according to example 1, in 4.5 ml of methanol and stirred for 25 hours at 50° C. Then, it is acidified with a 10% aqueous sulfuric acid to pH 5, diluted with ethyl acetate, shaken twice with semiconcentrated aqueous sodium chloride solution, dried with anhydrous sodium sulfate and concentrated by evaporation in a vacuum. The residue is chromatographed with diethyl ether/ethanol (99+1) on silica gel. In this way, 148 mg of the title compound is obtained as colorless oil.

IR: 3400, 2930, 2860, 1725, 1365, 1245, 992 $cm^{-1}$.

EXAMPLE 3

(+/-)-(5RS)-5-Acetoxy-5-[cis-(2RS)-2-((1E,3E)-(5RS)-5-hydroxy-1,3-(tridecadienyl)-(1RS)-cyclobutyl]-pentanoic acid Diastereomer polar (5)

6.6 ml of a 0.5 normal aqueous sodium hydroxide solution is added to a solution of 300 mg of the polar diastereomeric diacetate, produced according to example 1, in 6.6 ml of methanol at 23° C. and stirred for 0.75 hours at 23° C. under argon. Then, it is diluted with water and acidified at ice bath temperature with 10% aqueous sulfuric acid to pH 5. It is extracted with ethyl acetate, washed twice with semiconcentrated aqueous sodium chloride solution, dried with anhydrous sodium sulfate and concentrated by evaporation in a vacuum. The residue is chromatographed on silica gel. With diethyl ether/hexane (8+2), 202 mg of the title compound is obtained as colorless oil.

IR: 3600, 2925, 2858, 1729, 1712, 1700, 1250, 993, 960 $cm^{-1}$.

EXAMPLE 4

(±)-(5RS)-5-Hydroxy-5-[cis-(2RS)-2-((1E,3E)-(5RS)-5-hydroxy-1,3-tridecadienyl)-(1RS)-cyclobutyl]-pentan-1-ol Diastereomer polar (5)

360 mg of the polar diastereomeric diacetate (diastereomer polar (5)) described in example 1 is stirred for 60 hours at 24° C. with 11 ml of a solution of potassium hydroxide in water and ethanol (production: 5 g of potassium hydroxide is dissolved in 67.5 ml of water and 182.5 ml of ethanol).

Then, it is acidified with 10% aqueous citric acid solution to pH 6, extracted four times with 20 ml of dichloromethane each, the organic phase is shaken with semiconcentrated sodium chloride solution, dried on anhydrous magnesium sulfate and concentrated by evaporation in a vacuum. The residue is chromatographed with ethyl acetate on silica gel. In this way, 103 mg of the title compound is obtained as colorless oil.

IR: 3605, 3360 (broad), 2930, 2860, 993 cm$^{-1}$.

EXAMPLE 5

(±)-(5RS)-5-Acetoxy-5-[cis-(2RS)-2-((1E,3E)-(5RS)-5-acetoxy-1,3-tridecadienyl)-(1RS)-cyclobutyl]-pentanoic acid Diastereomer nonpolar (5), A For acetylation, 1 g of acetic anhydride is added to a solution of 0.61 g of the above-described nonpolar alcohol (diastereomer nonpolar (5), A) in 2.0 ml of pyridine and stirred for 22 hours at room temperature. Then, it is concentrated by evaporation in a vacuum while adding toluene and the residue is chromatographed on silica gel. With hexane/diethyl ether (9+1), 0.62 g of the acetate is obtained as colorless oil.

IR: 2930, 2860, 1726, 1606, 1374, 1252, 993, 840 cm$^{-1}$.

For silylether cleavage, 0.61 g of the above-produced acetate in 25 ml of tetrahydrofuran is stirred with 0.7 g of tetrabutylammonium fluoride for 20 minutes at 0° C. and for 4 hours at 24° C. under argon. Then, it is diluted with diethyl ether, washed three times with water, dried on anhydrous magnesium sulfate and concentrated by evaporation in a vacuum. The residue is chromatographed with diethyl ether/hexane (8+2) on silica gel. In this way, 1.3 g of the 1-alcohol is obtained as colorless oil.

IR: 3620, 3450, 2930, 2860, 1725, 1608, 1375, 1250, 990 cm$^{-1}$.

For oxidation of the 1-hydroxy group, 2.5 g of Collins reagent is added to 0.43 g of the above-produced alcohol in 50 ml of dichloromethane and stirred for 20 minutes at 0° C. Then, it is diluted with a mixture of hexane/diethyl ether (1+1), Celite is added, filtered, washed with hexane/diethyl ether (1+1) and concentrated by evaporation in a vacuum. The thus obtained 1-aldehyde is immediately processed further without further purification.

0.9 ml of Jones reagent (J. Chem. Soc. 1953, 2555) is instilled in a solution of 0.41 g of the above-produced aldehyde in 10 ml of acetone with stirring at −25° C. and stirred for 15 minutes at −25° C. under argon. Then, 2 ml of 2-propanol is added, stirred for 5 minutes, diluted with 60 ml of diethyl ether, shaken twice with semiconcentrated sodium chloride solution, dried on anhydrous sodium sulfate and concentrated by evaporation in a vacuum. The residue is chromatographed on silica gel. With diethyl ether/hexane (7+3), 374 mg of the title compound is obtained as colorless oil.

IR: 3520 (broad), 2930, 2859, 1725, 1372, 1250, 990 cm$^{-1}$.

The initial material for the above title compound is produced as follows:

EXAMPLE (±)-(5RS)-5-Hydroxy-5-[cis-(2RS)-2-((1E,3E)-(5RS)-5-hydroxy-1,3-tridecadienyl)-(1RS)-cyclobutyl]-pentanoic acid Diastereomer nonpolar (5) A Analogously to example 2, 124 mg of the title compound is obtained as colorless oil from 180 mg of the diacetate, produced according to example 5.

IR: 3400, 2930, 2858, 1725, 1360, 1250, 992, 930 cm$^{-1}$.

EXAMPLE 7

(±)-(5RS)-5-Acetoxy-5-[cis-(2RS)-2-((1E,3E)-(5RS)-5-hydroxy-1,3-tridecadienyl)-(1RS)-cyclobutyl]-pentanoic acid Diastereomer nonpolar (5) A Analogously to example 3, 123 mg of the title compound is obtained as colorless oil from 150 mg of the diacetate, produced according to example 5.

IR: 3600, 2930, 2860, 1721, 1252, 992, 962 cm$^{-1}$.

EXAMPLE 8

(±)-(5RS)-5-Hydroxy-5-[cis-(2RS)-2-((1E,3E)-(5RS)-5-hydroxy-1,3-tridecadienyl)-(1RS)-cyclobutyl]-pentan-1-ol Diastereomer nonpolar (5) A Analogously to example 4, 95 g of the title compound is obtained as colorless oil from 170 mg of the diacetate produced according to example 5.

IR: 3600, 3380 (broad), 2930, 2860, 992 cm$^{-1}$.

EXAMPLE 9

(±)-(5RS)-5-Acetoxy-5-[trans-(2RS)-2-((1E,3E)-(5RS)-5-acetoxy-1,3-tridecadienyl)-(1RS)-cyclobutyl]-pentanoic acid Diastereomer B A solution of 8.9 g of 4-chloro-1-(tert.-butyldimethylsilyloxy)-butane in 8 ml of tetrahydrofuran is instilled in 1.92 g of magnesium at 25° C. under argon, a crystal of iodine is added, heated for 10 minutes to 60° C. stirred for 30 minutes at 25° C. and diluted with 25 ml of tetrahydrofuran.

A solution of 4.0 g of trans-(1RS)-1-formyl-(2RS)-2-[(1E,3E)-(5RS)-5-acetoxy-1,3-tridecadienyl-cyclobutane in 40 ml of tetrahydrofuran is instilled in 25 ml of this magnesium-organic solution at −70° C. under argon and stirred for 0.5 hours at −70° C. It is mixed with 100 ml of saturated aqueous ammonium chloride solution, extracted with diethyl ether, the organic phase is shaken with semiconcentrated aqueous sodium chloride solution, dried on anhydrous sodium sulfate and concentrated by evaporation in a vacuum. The residue is chromatographed on silica gel. With hexane/ethyl acetate (85+15), 2 5-(tert.butyldimethylsilyloxy-1-trans-{2-[1E,3E-(5RS)-5-acetoxy-1,3-tridecandienyl]-cyclopentyl}-pentan-1-ol diastereomers in the sequence of increasing polarity.

1.94 g of nonpolar diastereomer A 1.7 g of polar diastereomer B

IR: 3430, 2932, 2859, 1725, 1372, 1256, 992, 839 cm$^{-1}$.

For acetylation, 1.0 ml of acetic anhydride is added to a solution of 0.9 g of the above-produced alcohol (diastereomer B) in 20 ml of pyridine and stirred for 21 hours at room temperature. Then, it is concentrated by evaporation in a vacuum while adding toluene and the residue is chromatographed on silica gel. With hexane/ethyl acetate (85+15), 0.97 g of the acetate is obtained as colorless oil.

IR: 2940, 2862, 1728, 1375, 1257, 992, 840 cm$^{-1}$.

For silylether cleavage, 0.93 g of the above-produced acetate in 36 ml of tetrahydrofuran is stirred with 1.1 g of tetrabutylammonium fluoride for 1 hour at 0° and for 3 hours at 24° C. under argon. Then, it is diluted with diethyl ether, washed three times with water, dried on anhydrous magnesium sulfate and concentrated by evaporation in a vacuum. The residue is chromatographed on silica gel. With hexane/ethyl acetate mixtures, 0.65 g of (±)-(5RS)-5-acetoxy-5-[trans-(2RS)-2-((1E,3E)-(5RS)-5-acetoxy-1,3-tridecadienyl)-(1RS)-cyclobutyl]pentan-1-ol is obtained as colorless oil.

IR: 3620, 3460, 2730, 2860, 1725, 1608, 1375, 1250, 992, 950 cm$^{-1}$.

For oxidation of the 1-hydroxy group, 3.8 g of Collins reagent is added to 0.64 g of the above-produced alcohol (diastereomer B) in 70 ml of dichloromethane at 0° C. and stirred for 20 minutes at 0° C. Then, it is diluted with a mixture of hexane/diethyl ether (1+1), Celite is added, filtered, washed with hexane/diethyl ether (1+1) and concentrated by evaporation in a vacuum. The thus obtained 1-aldehyde is immediately used without further purification.

1.3 ml of Jones reagent is instilled in a solution of 0.6 g of the above-produced aldehyde in 16 ml of acetone with stirring at −25° C. and stirred for 15 minutes at −25° C. under argon. Then, 3 ml of 2-propanol is added, stirred for 5 minutes, diluted with 100 ml of diethyl ether, shaken twice with semiconcentrated sodium chloride solution, dried on anhydrous sodium sulfate and concentrated by evaporation in a vacuum. The residue is chromatographed on silica gel. With hexane/ethyl acetate (6+4), 0.52 g of the title compound is obtained as colorless oil.

IR: 3520, 2930, 2860, 1725, 1658, 1360, 1250, 990, 946 cm$^{-1}$.

9a) 5-[trans-1-(tert.-Butyl-dimethylsilyloxymethyl)cyclobut-2-yl]-(2E,4E)-pentadienoic acid ethyl A solution of 20 g of trans-1,2-cyclobutanedicarboxylic acid dichloride in 40 ml of tetrahydrofuran is carefully instilled at −15° C. in a solution of 8.4 g of sodium borohydride in 280 ml of ethyl alcohol. After completion of the gas generation it is stirred for 30 minutes at −15° C. and then 150 ml of water is slowly instilled. It is stirred for 30 minutes at 22° C. and then diluted with 1.5 liter of diethyl ether. It is shaken twice with water, twice with semiconcentrated sodium chloride solution, dried on anhydrous sodium sulfate and concentrated by evaporation in a vacuum. The residue is purified by chromatography on silica gel. With ethyl acetate, 9.5 g of trans-1,2-dihydroxymethylcyclopentane is obtained as colorless liquid.

IR: 3610, 3400, 2960, 1062 cm$^{-1}$.

22.7 g of imidazole and 25.1 g of tert.-butyldimethylsilyl chloride are added to a solution of 19.3 g of trans-1,2-dihydroxymethyl-cyclopentane in 200 ml of dimethylformamide at 0° C. and stirred for 22 hours at 24° C. It is diluted with 1.5 l of diethyl ether, shaken twice with 80 ml of 10% aqueous sulfuric acid each, washed neutral with water, dried on anhydrous magnesium sulfate and concentrated by evaporation in a vacuum. The residue is chromatographed on silica gel. With hexane/ethyl acetate (8+2), 17 g of trans-1-(tert.-butyldimethylsilyloxymethyl)-2-hydroxymethyl-cyclopentane is obtained as colorless liquid.

IR: 3420, 2960, 2860, 1260, 840 cm$^{-1}$.

70 g of Collins reagent is added to a solution of 14.9 g of the above-described monosilylether in 750 ml of dichloromethane and stirred for 30 minutes at 0° C. Then, it is diluted with a mixture of hexane/diethyl ether (3+2), Celite is added, filtered and concentrated by evaporation in a vacuum. 13.8 g of the aldehyde is obtained, which is used without further purification.

IR: 2958, 2860, 2720, 1719, 840 cm$^{-1}$.

For Wittig-Horner olefination, 8 g of phosphonocrotonic acid triethyl ester and 4.9 g of diazabicycloundecene (DBU) are added at 24° C. to a stirred suspension of 1.37 g of lithium chloride in 250 ml of acetonitrile and stirred for 10 minutes. Then, a solution of 6.5 g of the above-described aldehyde in 50 ml of acetonitrile is instilled, stirred for 3.5 hours at 24° C. and then diluted with diethyl ether. It is shaken in succession with water, 10% aqueous citric acid solution and water, dried on anhydrous magnesium sulfate and concentrated by evaporation in a vacuum. The residue is chromatographed with hexane/ethyl acetate on silica gel. In this way, 5.9 g of the title compound is obtained as colorless oil.

IR: 2958, 2860, 1702, 1639, 1620, 1470, 1255, 1003, 840 cm$^{-1}$.

9b) 5-[trans-1-(tert.-Butyl-dimethylsilyloxymethyl)-cyclobut-2-yl]-(2E,4E)-pentadien-1-ol 33.5 ml of a 1.2 molar solution of diisobutylaluminum hydride in toluene is instilled in a solution of 5.2 g of the ester, produced according to example 9a, in 150 ml of toluene at −70° C. under argon and stirred for 30 minutes at −70° C. Then, 16 ml of 2-propanol and, after 5 minutes, 16 ml of water are instilled, stirred for 2 5 hours at 23° C. filtered washed with dichloromethane and concentrated by evaporation in a vacuum. The residue is purified by chromatography on silica gel. With hexane/diethyl ether (7+3), 4.85 g of the alcohol is obtained as colorless oil.

IR: 3610, 3450, 990, 840 cm$^{-1}$.

For aldehyde production, a solution of 4.8 g of the above-produced alcohol in 100 ml of toluene is mixed with 15 g of manganese dioxide and stirred for 3 hours at 24° C. Then, it is filtered, concentrated by evaporation and chromatographed on silica gel. With hexane/ethyl acetate (8+2), 4.5 g of the title compound is obtained as colorless oil.

IR: 2960, 2860, 2740, 1680, 1633, 990, 940, 840 cm$^{-1}$.

9c) (5RS)-5-Acetoxy-1-[trans-1-(tert.-butyldimethylsilyloxymethyl)-cyclobut- 2-yl]-1-(1E,3E)-tridecadiene A solution of 8.9 g of octyl bromide in 10 ml of diethyl ether is instilled in 1.12 g of magnesium in 4 ml of diethyl ether with heating and stirred for 30 minutes at 25° C.

A solution of 4.4 g of aldehyde, produced according to example 9b, in 50 ml of diethyl ether is instilled in 8.33 ml (=mmol) of this Grignard solution at −20° C. under argon and stirred for 45 minutes at −20° C. It is mixed with saturated ammonium chloride solution, extracted three times with diethyl ether, the organic phase is shaken with semiconcentrated sodium chloride solution, dried on anhydrous sodium sulfate and concentrated by evaporation in a vacuum. The residue is chromatographed on silica gel. With hexane/ethyl acetate (6+4), 6.1 g of alcohol (diastereomer mixture) is obtained as colorless oil.

For acetylation, 10 ml of acetic anhydride is added to a solution of 6.05 g of the above-produced alcohol in 20 ml of pyridine and stirred for 23 hours at room temperature. Then, it is concentrated by evaporation in a vacuum while adding toluene and the residue is chromatographed on silica gel. With hexane/ethyl acetate (9+1), 6.4 g of the title compound is obtained as colorless oil.

IR: 2938, 2860, 1725, 1658, 1255, 991, 945, 840 cm$^{-1}$.

9d) trans-(1RS)-1-Formyl-(2RS)-2-[(1E,3E)-(5RS)-5-acetoxy-1,3 -tridecadienyl]-cyclobutane 9.2 g of tetrabutylammonium fluoride is added to a solution of 6.3 g of the acetate, produced according to example 9c, in 160 ml of tetrahydrofuran at 0° C., stirred for 15 minutes at 0° C. and for 3 hours at 24° C. Then, it is diluted with 1 l of diethyl ether and washed three times with semiconcentrated aqueous sodium chloride solution. It is dried with anhydrous sodium sulfate, concentrated by evaporation in a vacuum and the residue is chromatographed on silica gel. With hexane/ethyl acetate (7+3), 4.4 g of the alcohol is eluted as colorless oil.

IR: 3625, 3450, 2932, 2862, 1728, 1680, 1250, 991 cm$^{-1}$.

28 g of Collins reagent is added to a solution of 4.3 g of the above-produced alcohol in 130 ml of dichloromethane at 0° C. and stirred for 20 minutes at 0° C. Then, it is diluted with a mixture of hexane/diethyl ether (1+1), Celite is added, filtered and concentrated by evaporation in a vacuum. The thus obtained aldehyde was used without further purification.

IR: 2930, 2860, 2721, 1721, 1250, 990 cm$^{-1}$.

EXAMPLE 10

(+/+)-(5RS)-5-Hydroxy-5-[trans-(2RS)-2-((1E,3E)-(5RS)-5-hydroxy-1,3-tridecadienyl)-(1RS)-cyclobutyl]-pentanoic acid Diastereomer B Analogously to example 2, 134 mg of the title compound is obtained as colorless oil from 180 mg of the diacetate, produced according to example 9.

IR (film): 3450, 2928, 2858, 1714, 1660, 1250, 989, 30 cm$^{-1}$.

EXAMPLE 11

(±)-(5RS)-5-Acetoxy-5-[trans-(2RS)-2-((1E,3E)-(5RS)-5-hydroxy-1,3-tridecadienyl)-(1RS)-cyclobutyl]-pentanoic acid Diastereomer B Analogously to example 3, 46 mg of the title compound is obtained as colorless oil from 200 mg of the diacetate, produced according to example 9.

IR (film): 3450, 2930, 2860, 1730, 1710, 1660, 1275, 990 cm$^{-1}$.

EXAMPLE 12

(±)-(5RS)-5-Acetoxy-5-[trans-(2RS)-2-((1E,3E)-(5RS)-5-acetoxy-1,3-tridecadienyl)-(1RS)-cyclobutyl]-pentanoic acid Diastereomer A 3.8 g of Collins reagent is added to a solution of 0.64 g of the 1-alcohol from the nonpolar alcohol (diastereomer A), produced according to example 9 by acetylation and silylether cleavage in 70 ml of dichloromethane at 0° C. and stirred for 20 minutes at 0° C. Then, it is diluted with a mixture of hexane/diethyl ether (1+1), Celite is added, filtered, washed with hexane/diethyl ether (1+1) and concentrated by evaporation in a vacuum. The thus obtained 1-aldehyde is immediately used without further purification.

1.3 ml of Jones reagent is instilled in a solution of 0.6 g of the above-produced aldehyde in 16 ml of acetone with stirring at −25° C. and stirred for 12 minutes at −25° C. under argon. Then, 3 ml of 2-propanol is added, stirred for 5 minutes, diluted with diethyl ether, shaken with semiconcentrated aqueous sodium chloride solution, dried on anhydrous sodium sulfate and concentrated by evaporation in a vacuum. The residue is chromatographed on silica gel. With hexane/ethyl acetate (6+4), 0.52 g of the title compound is obtained as colorless oil.

IR: 3520, 2930, 2860, 1724, 1658, 1373, 1250, 989, 946 cm$^{-1}$.

EXAMPLE 13

(±)-(5RS)-5-Hydroxy-5-[trans-(2RS)-2-((1E,3E)-(5RS)-5-hydroxy-1,3-tridecadienyl)-(1RS)-cyclobutyl]-pentanoic acid Diastereomer A Analogously to example 2, 153 mg of the title compound is obtained as colorless oil from 200 mg of the diacetate, produced according to example 12.

IR: 3600, 3420, 2930, 2859, 1730, 1660, 1250, 990 cm$^{-1}$.

EXAMPLE 14

(±)-(5RS)-5-Acetoxy-5-[trans-(2RS)-2-((1E,3E)-(5RS)-5-hydroxy-1,3-tridecadienyl)-(1RS)-cyclobutyl]-pentanoic acid Diastereomer A Analogously to example 3, 174 mg of the title compound is obtained as colorless oil from 200 mg of the diacetate, produced according to example 12.

IR (film): 3610, 3450, 2930, 2860, 1724, 1660, 1250, 990 cm$^{-1}$.

EXAMPLE 15

(±)-(5RS)-5-Hydroxy-5-[cis-(2RS)-2-((1E,3E)-(5RS)-5-hydroxy-1,3-tridecadienyl)-(1RS)-cyclobutyl]-pentanoic acid methyl ester Diastereomer polar (5)

An ethereal diazomethane solution is instilled in a solution of 100 mg of the acid, produced according to example 2, in 10 ml of dichloromethane at 0° C. until permanent yellow coloring and stirred for 15 minutes at 0° C. Then, it is concentrated by evaporation in a vacuum and the residue is chromatographed on silica gel. With hexane/ethyl acetate (2+8), 69 mg of the title compound is obtained as colorless oil.

IR (film): 3600, 2925, 2855, 1738, 1658, 990 cm$^{-1}$.

EXAMPLE 16

(±)-(5RS)-5-Hydroxy-5-[cis-(2RS)-2-((1E,3E)-(5RS)-5-hydroxy-1,3-tridecadienyl)-(1RS)-cyclobutyl]-pentanoic acid methyl ester Diastereomer nonpolar (5) A Analogously to example 15, 95 mg of the title compound is obtained as oil from 110 mg of the acid, produced according to example 6.

IR (film): 3610, 2925, 2855, 1738, 1660, 990 cm$^{-1}$.

EXAMPLE 17

(±)-(5RS)-5-Acetoxy-5-[cis-(2RS)-2-((1E,3E)-(5RS)-5-hydroxy-1,3-tridecadienyl)-(1RS)-cyclobutyl]-pentanoic acid methyl ester Diastereomer polar (5)

Analogously to example 15, 71 mg of the title compound is obtained as colorless oil from 70 mg of the acid, produced according to example 3.

IR (film): 3400, 2924, 2858, 1739, 1658, 1240, 990 cm$^{-1}$.

EXAMPLE 18

(±)-(5RS)-5-Hydroxy-5-[cis-(2RS)-2-((1E,3E)-(5RS)-5-hydroxy-1,3-tridecadienyl)-(1RS)-cyclobutyl]-pentanoic acid-tris-(hydroxymethyl)- aminomethane salt Diastereomer polar (5)

A solution of 15 mg of tris-(hydroxymethyl)-aminomethane in 0.03 ml of water is added to a solution of 40 mg of the carboxylic acid, produced according to example 2, in 6 ml of acetonitrile at 70° C. It is allowed to cool with stirring, is decanted after 16 hours from the solvent and the residue is dried in a vacuum. 16 mg of the title compound is isolated as waxy mass.

EXAMPLE 19

(±)-(5RS)-5-Hydroxy-5-[cis-(2RS)-2-((1E,3E)-(5RS)-5-hydroxy-1,3-tridecadienyl)-(1RS)-cyclobutyl]-pentanoic acid-1,5-lactone Diastereomer polar (5)

0.9 g of anhydrous magnesium sulfate is added to a solution of 53 mg of the carboxylic acid, produced according to example 6, in 9 ml of toluene at 24° C. over a period of 24 hours in portions and stirred for another 24 hours at 24° C. Then, it is filtered and the evaporation residue is chromatographed on silica gel. With toluene/ethyl acetate (7+3), 28 mg of the 1,5-lactone is eluted as colorless oil.

IR: 3600, 2930, 2860, 1729, 1250, 990 $cm^{-1}$.

EXAMPLE 20

(±)-(5RS)-5-Acetoxy-5-[cis-(2RS)-2-((1E,3E)-(5R or 5S)-5-acetoxy-1,3-tridecadienyl)-(1RS)-cycloheptyl]-pentanoic acid (diastereomer A)

A solution of 1.09 g of 4-chlor-1-(tert.-butyldimethylsilyloxy)-butane in 1 ml of tetrahydrofuran is instilled in 238 mg of magnesium at 24° C. under argon, a crystal of iodine is added, heated for 10 minutes to 70° C., stirred for 30 minutes at 24° C. and diluted with 3 ml of tetrahydrofuran.

The above-produced Grignard solution is instilled in a solution of 467 mg of cis-(1RS)-1-formyl(2RS)-2-[(1E,3E)-(5R or 5S)-5-acetoxy-1,3-tridecadienyl-cycloheptane (diastereomer A) from example 1e) in 2.6 ml of tetrahydrofuran at −70° C. under argon, it is allowed to warm to −30° C. and is stirred for 1 hour at this temperature. The reaction mixture is added to 100 ml of saturated ammonium chloride solution and extracted three times each with 100 ml ethyl acetate. The combined organic phases are washed once with semiconcentrated aqueous sodium chloride solution, dried on anhydrous sodium sulfate and, after filtration, concentrated by evaporation in a vacuum. The thus obtained residue is purified by chromatography on silica gel. With hexane/methyl-tert.-butyl ether (92+8), 351 mg of 5-(tert.-butyldimethylsilyloxy)- 1-cis-{2-[(1E,3E)-(5RS)-5-acetoxy-1,3-tridecadienyl]-cycloheptyl)-pentan-1-ol is obtained as colorless oil.

IR ($CHCl_3$): 3690, 3610, 3440 (broad), 3005, 2932, 2860, 1727, 1465, 1375, 1247, 1098, 995, 840 $cm^{-1}$.

For acetylation, 0.5 ml of acetic anhydride is added to a solution of 345 g of the above-described alcohol in 1 ml of pyridine and stirred for 6 hours at 24° C. Then, it is diluted with water and concentrated by evaporation in a vacuum while adding toluene. The thus obtained residue is purified by chromatography on silica gel. With hexane/0–10%ethyl acetate, 347 mg of the acetate is obtained as colorless oil.

IR ($CHCl_3$): 3002, 2930, 2860, 1725, 1464, 1374, 1243, 1100, 992, 838 $cm^{-1}$.

For silylether cleavage, 344 mg of the above-produced acetate in 2.3 ml of tetrahydrofuran is stirred with 366 mg of tetrabutylammonium fluoride trihydrate for 3 hours at 24° C. under argon. Then, it is diluted with 100 ml of diethylether, washed three times each with 20 ml of water, once with saturated aqueous sodium chloride solution, dried on anhydrous sodium sulfate and, after filtration, concentrated by evaporation in a vacuum. 314 mg of (+/−)-(5RS)-5-acetoxy-5-[cis-(2RS)-2-((1E,3E)-(5RS)-5 -acetoxy-1,3-tridecadienyl)-(1RS)-cycloheptyl]-pentan-1-ol is obtained as oil. The latter is dissolved without further purification in 15.5 ml of dichloromethane, mixed under argon at 0° C. with 2.63 g of Collins reagent (bis-pyridin-chromium(VI)-oxide complex, Tetrahedron Letters 1968, 3363) and stirred for 1 hour at 0° C. Then it is diluted with diethyl ether, mixed with Celite, filtered off over Celite and rewashed well with diethyl ether. The 1-aldehyde obtained after concentration by evaporation is immediately dissolved without further purification in 13.8 ml of acetone, mixed at −30° C. under argon with 0.35 ml of Jones reagent (chromium(VI)oxide in $H_2SO_4$) (J. Chem. Soc. 1953, 2555) and stirred for 20 minutes at this temperature. Then 0.15 ml of 2-propanol is added, stirred for 10 minutes, diluted with 70 ml of ethyl acetate, shaken four times with 20 ml of semiconcentrated aqueous sodium chloride solution each, dried on anhydrous sodium sulfate and, after filtration, concentrated by evaporation in a vacuum. The thus obtained residue is purified by chromatography on silica gel. With hexane/0–50% ethyl acetate, 117 mg of the title compound is obtained as colorless oil.

IR (film): 3450, 3190 (broad), 3022, 2925, 2855, 1737, 1710, 1456, 1370, 1240, 990 $cm^{-1}$.

The initial material for the above title compound is produced as follows:

20a) cis-1,2-bis-(hydroxymethyl)-cycloheptane 13.0 g of cis-1,2-cycloheptanedicarboxylic acid anhydride (J. Sicher et al., Collection Czechoslov. Chem. Commun. 26, 262 (1961) is dissolved in 13.8 ml of toluene and 18.8 ml of methanol. After addition of 128 mg of p-toluene sulfonic acid, it is refluxed for 20 hours. After concentration by evaporation, the residue is taken up in 18.8 ml of methanol and refluxed again for 20 hours. After concentration by evaporation, the thus obtained residue is dissolved in 950 ml of toluene and mixed with 350 ml of a 1.2 molar solution of diisobutylaluminum hydride at −78° C. under argon. It is allowed to heat for 2 hours to 0° C., then 50 ml of isopropanol, drop by drop followed by 175 ml of water, is carefully added at −70° C. and then stirred for 2 hours at 24° C. It is filtered off from the precipitate, washed well with ethyl acetate and concentrated by evaporation in a vacuum. The thus obtained residue is purified by chromatography on silica gel. With hexane/0–70% ethyl acetate, 6.67 g of the title compound is obtained as colorless oil.

IR($CHCl_3$): 3625, 3370 (broad), 3005, 2930, 2862, 1460, 1380, 1075, 1040 $cm^{-1}$.

20b) 5-[cis/trans-1-(tert.-butyl-dimethylsilyloxymethyl)cyclohept- 2-yl]-(2E,4E)-2,4-pentadienoic acid ethyl ester A solution of 14.9 g of the above-produced diol in 10 ml of tetrahydrofuran is carefully instilled in a suspension of 4.1 g of sodium hydride (55% in mineral oil) in 180 ml of tetrahydrofuran at 0° C. under argon. It is stirred for 45 minutes at 24° C. and then 14.1 g of tert.-butyl-dimethylsilyl chloride is added at 0° C. It is stirred for one hour at 24° C. and diluted with 1000 ml of ether. The organic phase is washed with 200 ml of 10% aqueous potassium carbonate solution and four times with 100 ml of saturated aqueous sodium chloride solution each. After drying on anhydrous magnesium sulfate and filtration it is concentrated by evaporation in a vacuum. The thus obtained residue is purified by chromatography on silica gel. With hexane/0–30% ethyl acetate, 22.7 g of cis-1-tert.-butyldimethylsilyloxymethyl)-2-hydroxymethyl-cycloheptane is obtained as colorless oil.

IR(CHCl$_3$): 3420 (broad), 3008, 2937, 2862, 1470, 1262, 1060, 843 cm$^{-1}$.

19.5 g of dimethylsulfoxide dissolved in 42.6 ml of dichloromethane is carefully instilled in 14.8 g of oxalylchloride dissolved in 104 ml of dichloromethane at –60° C. under argon and stirred for 10 minutes at this temperature. Then a solution of 22.7 g of the above-produced alcohol in 42.6 ml of dichloromethane is instilled and stirred for 1 hour at –60° C. Then 26.3 g of triethylamine is added and, after 1 hour of stirring at –60° C., the reaction mixture is added to 300 ml of ice water. After phase separation the aqueous phase is extracted three times with 300 ml of dichloromethane each. The combined organic phases are washed neutral with 100 ml of 10% aqueous citric acid and then with semiconcentrated aqueous sodium chloride solution. After drying on magnesium sulfate and filtration it is concentrated by evaporation in a vacuum. 22.9 g of the aldehyde is obtained that is used without further purification.

IR(CHCl$_3$): 3005, 2935, 2862, 2740, 1720, 1475, 1258, 1100, 840 cm$^{-1}$.

36.6 g of 4-phosphonocrotonic acid triethyl ester followed by 12.9 g of DBU (diazabicycloundecane) is instilled in a suspension of 4.31 g of lithium chloride in 430 ml of acetonitrile at 24° C. under argon and stirred for 10 minutes at this temperature. Then a solution of 22.9 g of the above-produced aldehyde in 69 ml of acetonitrile is slowly instilled and stirred for 5 hours at 24° C. Then it is diluted with 1.5 l of diethyl ether, the phases are separated, the organic phase is washed in succession with 100 ml of water and 10% aqueous citric acid. After washing neutral with semiconcentrated aqueous sodium chloride solution and drying on anhydrous magnesium sulfate, it is concentrated by evaporation after filtration. The thus obtained residue is purified by chromatography on silica gel. With hexane/0–10% diethyl ether, 14.53 g of the title compound is obtained as colorless oil.

IR(CHCl$_3$): 30430, 2940, 2870, 1710, 1645, 1622, 1470, 1378, 1310, 1255, 1100, 1008, 843 cm$^{-1}$.

20c) 5-[cis/trans-1-(tert.-butyl-dimethylsilyloxymethyl)cyclohept- 2-yl]-(2E,4E)-2,4-pentadien-1-al 102 ml of a 1.2 molar solution of diisobutylaluminum hydride in toluene is instilled in a solution of 14.5 g of the above-produced ester in 270 ml of toluene at –70° C. under argon and allowed to heat to 0° C. within 2 hours. 5 ml of 2-propanol followed by 51 ml of water is carefully added at –70° C. and then stirred for 2 hours at 24° C. It is filtered off from the precipitate, washed well with ethyl acetate and concentrated by evaporation in a vacuum. The thus obtained residue is purified by chromatography on silica gel. With hexane/0–10% ethyl acetate, 9.22 g of 5-[cis/trans-1-(tert.-butyldimethylsilyloxymethyl)-cyclohept- 2-yl]-(2E,4E)-2,4-pentadien-1-ol is obtained as colorless oil.

IR(CHCl$_3$): 3420 (broad), 2940, 2865, 1630, 1465, 1100, 995, 840 cm$^{-1}$.

A solution of 9.21 g of the above-produced alcohol in 107 ml of dichloromethane is mixed with 19.7 g of manganese dioxide and stirred for 18 hours at 24° C. under argon. Then it is filtered and concentrated by evaporation in a vacuum. 8.57 g of the title compound is obtained as colorless oil, which is used without further purification.

IR(CHCl$_3$): 3005, 2935, 2863, 2748, 1680, 1637, 1603, 1467, 1260, 1100, 990, 840 cm$^{-1}$.

20d) (5R or 5S)-5-Acetoxy-1-[cis-1-hydroxymethyl-cyclohept-2-yl]-(1E,3E)-trideca-1,3-diene (diasteroemer A)

A solution of 6.15 g of octyl bromide in 50 ml of tetrahydrofuran is instilled in 774 mg of magnesium in 50 ml of tetrahydrofuran with heating and stirred for 30 minutes at 24° C. This Grignard solution is instilled in a solution of 8.56 g of the aldehyde produced in 1c) in 50 ml of tetrahydrofuran at –30° C. under argon and stirred for 30 minutes at this temperature. After heating to –10° C. the reaction mixture is added to 500 ml of saturated aqueous ammonium chloride solution. It is extracted three times with 300 ml of ethyl acetate each and the combined organic phases are then washed with saturated aqueous sodium chloride solution. After drying on anhydrous magnesium sulfate and filtration, it is concentrated by evaporation in a vacuum. The thus obtained residue is purified by chromatography on silica gel. With hexane/0–20% diethyl ether, 7.40 g of (5RS)-5-hydroxy-1-[cis/trans-1-(tert.-butyl-dimethylsilyloxymethyl)-cyclohept-2 -yl]-(1E,3E)-trideca-1,3-diene is obtained as colorless oil.

IR(CHCl$_3$): 3700, 3520 (broad), 3005, 2932, 2860, 1465, 1095, 992, 840 cm$^{-1}$.

A solution of 7.39 g of the above-produced alcohol in 26.6 ml of pyridine is mixed with 13.3 ml of acetic anhydride at 0° C. under argon and stirred at this temperature for 16 hours. Then it is mixed with 50 ml of water and concentrated by evaporation in a vacuum with addition of toluene. The thus obtained residue is purified by chromatography on silica gel. With hexane/0–5% diethyl ether, 8.1 g of (5RS)-5-acetoxy-1-[cis/trans-1-(tert.-butyl-dimethylsilyloxymethyl)-cyclohept- 2-yl]-(1E,3E)-trideca-1,3-diene is obtained as colorless oil.

IR(CHCl$_3$): 3005, 2930, 2860, 1725, 1465, 1375, 1253, 1095, 992, 840 cm$^{-1}$.

12.1 g of tetrabutylammonium fluoride trihydrate is added in a solution of 8.1 of the above-produced acetate in 77.5 ml of tetrahydrofuran at 24° C. under argon and stirred at this temperature for three hours. Then it is diluted with 500 ml of diethyl ether, washed three times each with 100 ml of water and once with saturated aqueous sodium chloride solution. After drying on anhydrous magnesium sulfate and filtration, it is concentrated by evaporation in a vacuum. The thus obtained residue is separated by multiple chromatography on silica gel. With hexane/ethyl acetate (85+15), four fractions (classified according to increasing polarity) are obtained.

1st fraction: 1.63 g of (5R or 5S)-5-acetoxy-1-[trans-1 -hydroxymethyl-cyclohept-2-yl]-(1E,3E)-trideca-1,3-diene (diastereomer A)

IR(CHCl$_3$): 3625, 3460 (broad), 3005, 2935, 2862, 1730, 1468, 1378, 1253, 1020, 995 cm$^{-1}$.

2nd fraction: 517 mg of the title compound

IR(CHCl$_3$): 3620, 3450 (broad), 3005, 2930, 2860, 1725, 1458, 1375, 1252, 1017, 992 cm$^{-1}$.

3rd fraction: 1.36 g of (5S or 5R)-5-acetoxy-1-[trans-1 -hydroxymethyl-cyclohept-2-yl]-(1E,3E)-trideca-1,3-diene (diastereomer B)

IR(CHCl$_3$): 3620, 3450 (broad), 3005, 2930, 2860, 1728, 1465, 1375, 1248, 1017, 990 cm$^{-1}$.

4th fraction: 767 mg of (5S or 5R)-5-acetoxy-1-[cis-1 -hydroxymethyl-cyclohept-2-yl]-(1E,3E)-trideca-1,3-diene (diastereomer B of the title compound)

IR(CHCl$_3$): 3620, 3450 (broad), 3005, 2930, 2860, 1728, 1460, 1375, 1250, 1017, 992 cm$^{-1}$.

20e) cis-(1RS)-1-Formyl-(2RS)-2-((1E,3E)-(5R or 5S)-5 -acetoxy-1,3-tridecadienyl)-cycloheptane (diastereomer A)

2.21 g of Collins reagent is added to a solution of 501 mg of the alcohol produced according to example 1d) in 37 ml of dichloromethane at 0° C. under argon and stirred for 80 minutes at 0° C. Then it is diluted with diethyl ether and mixed with Celite, filtered off on Celite and washed well with diethyl ether. After concentration by evaporation in a vacuum, the thus obtained title compound is used without further purification.

IR(CHCl$_3$): 3005, 2935, 2860, 2740, 1725, 1460, 1375, 1250, 990 cm$^{-1}$.

EXAMPLE 22

(±)-(5RS)-5-Acetoxy-5-[cis-(2RS)-2-((1E,3E)- (5R or 5S)-5 -hydroxy-1,3-tridecadienyl-(1RS)- cycloheptyl]-pentanoic acid (diastereomer A)

0.9 ml of a 0.5N aqueous sodium hydroxide solution is added to a solution of 44.3 mg of the diacetate, produced in example 1), in 0.9 ml of methanol and stirred for 2 hours at 24° C. Then it is mixed with 20 ml of water and adjusted to pH 5 with a 1N aqueous hydrochloric acid. Then it is extracted three times each with 30 ml of ethyl acetate, the combined organic phases are washed with 10 ml saturated aqueous sodium chloride solution, dried on sodium sulfate and after filtration concentrated by evaporation in a vacuum. The thus obtained residue is purified by chromatography on silica gel. With hexane/0–90% ethyl acetate, 34.3 mg of the title compound is obtained as colorless oil.

IR(film): 3430 (broad), 3020, 2925, 2855, 1735, 1710, 1456, 1371, 1242, 990 cm$^{-1}$.

EXAMPLE 22

(±)-(5RS)-5-Hydroxy-5-[cis-(2RS)-2-((1E,3E)- (5R or 5S)-5 -hydroxy-1,3-tridecadienyl-(1RS)- cycloheptyl]-pentanoic acid (diastereomer A) and (+/-)-(5RS)-5-hydroxy-5-[cis-(2RS)-2-((1E, 3E)-(5R or 5S)-5-hydroxy-1,3-tridecadienyl- (1RS)-cycloheptyl]-pentanoic acid-1,5-lactone (diastereomer A)

4.3 ml of a 1N aqueous sodium hydroxide solution is added to a solution of 68.5 mg of the diacetate, produced in example 1), in 2.85 ml of methanol and stirred for 18 hours at 24° C. Then it is mixed with 30 ml of water, washed once with ethyl acetate and the pH of the aqueous phase is adjusted to 5 with a 1N aqueous hydrochloric acid. Then it is extracted three times each with 30 ml of ethyl acetate, the combined organic phases are washed with 20 ml of semi-concentrated sodium chloride solution, dried on anhydrous sodium sulfate and after filtration concentrated by evaporation in a vacuum. The thus obtained residue is purified by chromatography on silica gel. With hexane/0–100% ethyl acetate, as nonpolar component 19.7 mg of (+/-)-(5RS)-5-hydroxy-5-[cis-(2RS)-2-((1E,3E)-(5R or 5S)-5-hydroxy-1, 3-tridecadienyl-(1RS)-cycloheptyl]-pentanoic acid-1,5-lactone (diastereomer A) and as more polar component 4.8 mg of (+/-)-(5RS)-5-hydroxy-5-[cis-(2RS)-2-((1E,3E)-(5R or 5S)-5-hydroxy-1,3-tridecadienyl-(1RS)-cycloheptyl]-pentanoic acid (diastereomer A) are obtained as colorless oils.

IR (Film; lactone): 3440 (broad), 3020, 2927, 2855, 1733, 1460, 1377, 1242, 991 cm$^{-1}$.

IR (CHCl$_3$; acid): 3440 (broad), 3005, 2925, 2860, 1725, 1462, 1380, 1240, 990 cm$^{-1}$.

EXAMPLE 23

(±)-(5R or 5S)-5-Acetoxy-5-[cis-(2RS)-2-((1E, 3E)-(5S or 5R)-5-acetoxy-1,3-tridecadienyl- (1RS)-cycloheptyl]-pentanoic acid (diastereomer B, nonpolar 5)

A solution of 1.39 g of 4-chloro-1-(tert.butyldimethylsilyloxy)-butane in 1.2 ml of tetrahydrofuran is instilled in 303 mg of magnesium at 24° C. under argon, a crystal of iodine is added, heated for 10 minutes to 70° C. stirred for 30 minutes at 24° C. and diluted with 3.9 ml of tetrahydrofuran.

The above-produced Grignard solution is instilled in a solution of 595 mg of cis-(1RS)-1-formyl-(2RS)-2-[(1E, 3E)-(5S or 5R)-5-acetoxy-1,3-tridecadienyl-cycloheptane (diastereomer B) from example 4a) in 3.3 ml of tetrahydrofuran at –70° C. under argon and allowed to heat to –30° C. and stirred for 1 hour at this temperature. The reaction mixture is added to 100 ml of saturated ammoniumchloride solution and extracted three times with ethyl acetate. The combined organic phases are washed once with semiconcentrated aqueous sodium chloride solution, dried on anhydrous sodium sulfate and after filtration concentrated by evaporation in a vacuum. The thus obtained residue is purified by multiple chromatography on silica gel. With hexane/ethyl acetate (90+10), 131.4 mg of the nonpolar diastereomer alcohol (nonpolar 5) and 404.7 mg of the more polar diastereomer alcohol (polar 5) are obtained as colorless oil.

IR (film; nonpolar alcohol): 3650, 3460 (broad), 3022, 2925, 2865, 1734, 1462, 1370, 1248, 1100, 990, 835 cm$^{-1}$.

IR (film; polar alcohol): 3650, 3460 (broad), 3025, 2930, 2857, 1735, 1237, 1460, 1372, 1100, 990, 836 cm$^{-1}$.

For acetylation 0.2 ml of acetic anhydride is added to a solution of 129 mg of the above-described nonpolar alcohol in 0.4 ml of pyridine and stirred for 6 hours at 24° C. Then it is concentrated by evaporation in a vacuum with addition of toluene. The thus obtained residue is purified by chromatography on silica gel. With hexane/0–10% ethyl acetate, 81.2 mg of the acetate is obtained as colorless oil.

IR(CHCl$_3$): 3005, 2930, 2860, 1725, 1465, 1375, 1255, 992, 838 cm$^{-1}$.

For silylether cleavage 77.2 mg of the above-produced acetate in 0.5 ml of tetrahydrofuran is stirred with 91.3 mg of tetrabutylammonium fluoride trihydrate at 24° C. under argon for 3 hours. Then it is diluted with 70 ml of diethyl ether, washed three times with 20 ml of water each, once with saturated aqueous sodium chloride solution, dried on anhydrous sodium sulfate and, after filtration, concentrated by evaporation in a vacuum. After filtration on silica gel with hexane/ethyl acetate, 47.1 mg of 1-alcohol is obtained as colorless oil. The alcohol is dissolved in 6 ml of ethyl acetate and stirred with addition of 440 mg of platinum(IV)oxide in an oxygen atmosphere for 4 hours. Then it is suctioned off from the catalyst and concentrated by evaporation in a vacuum. The thus obtained residue is purified by chromatography on silica gel. With hexane/0–50% ethyl acetate, 41.3 mg of the title compound is obtained as colorless oil.

IR(CHCl$_3$): 3625, 3490 (broad), 3005, 2930, 2860, 1725, 1468, 1373, 1252, 992 cm$^{-1}$.

The initial material for the above title compound is produced as follows:

23a) cis-(1RS)-1-Formyl-(2RS)-2-((1E,3E)-(5S or 5R)-5 -acetoxy-1,3-tridecadienyl)-cycloheptane (diastereomer B)

Analogously to example 1e) 595 mg of the title compound is obtained from 753 mg of (5S or 5R)-5-acetoxy-1-[cis-1 -hydroxymethyl-cyclohept-2-yl]-(1E,3E)-trideca-1,3-diene (diastereomer B, 4th fraction from example 1d)), that is used without further purification.

IR(CHCl$_3$): 3005, 2935, 2858, 2742, 1725, 1460, 1372, 1250, 990 cm$^{-1}$.

EXAMPLE 24

(±)-(5S or 5R)-5-Acetoxy-5-[cis-(2RS)-2-((1E, 3E)-(5S or 5R)-5-acetoxy-1,3-tridecadienyl-(1RS)-cycloheptyl]-pentanoic acid (diastereomer B, polar 5)

For acetylation 0.6 ml of acetic anhydride is added to a solution of 400 mg of polar alcohol, obtained in example 23, in 1.2 ml pyridine and stirred for 6 hours at 24° C. Then it is concentrated by evaporation in a vacuum with addition of toluene. The thus obtained residue is purified by chromatography on silica gel. With hexane/0–10% ethyl acetate, 322.7 mg of acetate is obtained as colorless oil.

IR(CHCl$_3$): 3005, 2930, 2858, 1725, 1464, 1375, 1253, 992, 838 cm$^{-1}$.

For silylether cleavage 318.7 mg of the above-produced acetate in 2.1 ml of tetrahydrofuran is stirred with 376.7 mg of tetrabutylammonium fluoride trihydrate at 24° C. under argon for 3 hours. Then it is diluted with 150 ml of diethyl ether, washed three times with 30 ml of water each, once with saturated aqueous sodium chloride solution, dried on anhydrous sodium sulfate and, after filtration, concentrated by evaporation in a vacuum. After filtration on silica gel with hexane/ethyl acetate, 198 mg of 1-alcohol is obtained as colorless oil. The alcohol is dissolved in 26 ml of ethyl acetate and stirred with addition of 1.95 g of platinum(IV)oxide in an oxygen atmosphere for 4 hours. Then it is suctioned off from the catalyst and concentrated by evaporation in a vacuum. The thus obtained residue is purified by chromatography on silica gel. With hexane/0–50% ethyl acetate, 200 mg of the title compound is obtained as colorless oil.

IR(CHCl$_3$): 3625, 3480 (broad), 3005, 2930, 2860, 1725, 1465, 1373, 1250, 990 cm$^{-1}$.

EXAMPLE 25

(±)-(5R or 5S)-5-Acetoxy-5-[cis-(2RS)-2-((1E, 3E)-(5S or 5R)-5-hydroxy-1,3-tridecadienyl-(1RS)-cycloheptyl]-pentanoic acid (diastereomer B, nonpolar 5)

Analogously to example 21, 18.7 mg of the title compound is obtained as colorless oil from 41 mg of (±)-(5R or 5S)-5-acetoxy-5-[cis-(2RS)-2-((1E,3E)-(5S or 5R)-5-acetoxy-1,3-tridecadienyl-(1RS)-cycloheptyl]-pentanoic acid (diastereomer B, nonpolar 5) from example 4).

IR (film): 3440 (broad), 3020, 2928, 2858, 1737, 1713, 1458, 1375, 1442, 990 cm$^{-1}$.

EXAMPLE 26

(±)-(5S or 5R)-5-Acetoxy-5-[cis-(2RS)-2-((1E, 3E)-(5S or 5R)-5-hydroxy-1,3-tridecadienyl-(1RS)-cycloheptyl]-pentanoic acid (diastereomer B, polar 5)

Analogously to example 21, 62.4 mg of the title compound is obtained as colorless oil from 80 mg of (±)-(5S or 5R)-5-acetoxy-5-[cis-(2RS)-2-((1E,3E)-(5S or 5R)-5-acetoxy-1,3-tridecadienyl-(1RS)-cycloheptyl]-pentanoic acid (diastereomer B, polar 5) from example 5).

IR (film): 3415, 3100 (broad), 3015, 2920, 2848, 1727, 1695, 1465, 1375, 1255, 990 cm$^{-1}$.

EXAMPLE 27

(±)-(5S or 5R)-5-Hydroxy-5-[cis-(2RS)-2-((1E, 3E)-(5S or 5R)-5-hydroxy-1,3-tridecadienyl-(1RS)-cycloheptyl]-pentanoic acid (diastereomer B, polar 5) and (+/-)-(5S or 5R)-5-hydroxy-5-[cis-(2RS)-2-((1E,3E)-(5S or 5R)-5-hydroxy-1,3-tridecadienyl-(1RS)-cycloheptyl]-pentanoic acid-1,5-lactone (diastereomer B, polar 5)

Analogously to example 22, 42.6 mg of (+/-)-(5S or 5R)-5-hydroxy-5-[cis-(2RS)-2-((1E,3E)-(5S or 5R)-5-hydroxy-1,3-tridecadienyl-(1RS)-cycloheptyl]-pentanoic acid-1,5-lactone (diastereomer B, polar 5) in a more nonpolar fraction and 3.5 mg of (±)-(5S or 5R)-5-hydroxy-5-[cis-(2RS)-2-((1E,3E)-(5S or 5R)-5-hydroxy-1,3-tridecadienyl-(1RS)-cycloheptyl]-pentanoic acid (diastereomer B, polar 5) in a more polar fraction are obtained as colorless oil from 120 mg of (±)-(5S or 5R)-5-acetoxy-5-[cis-(2RS)-2-((1E,3E)-(5S or 5R)-5-acetoxy-1,3-tridecadienyl-(1RS)-cycloheptyl]-pentanoic acid (diastereomer B, polar 5) from example 5).

IR (film; lactone): 3445 (broad), 3020, 2928, 2858, 1735, 460, 1242, 990 cm$^{-1}$.

IR (CHCl$_3$); acid): 3450 (broad), 3005, 2930, 2860, 1730, 462, 1375, 1250, 990 cm$^{-1}$.

EXAMPLE 28

(±)-(5RS)-5-Acetoxy-5-[trans-(2RS)-2-((1E,3E)-(5R or 5S)-5-acetoxy-1,3-tridecadienyl-(1RS)-cycloheptyl]-pentan-1-ol (diastereomer A)

A solution of 2.93 g of 4-chloro-1-(tert.-butyldimethylsilyloxy)-butane in 2.5 ml of tetrahydrofuran is instilled in 639 mg of magnesium at 24° C. under argon, a crystal of iodine is added, heated for 10 minutes to 70° C., stirred for 30 minutes at 24° C. and diluted with 8.2 ml of tetrahydrofuran.

The above-produced Grignard solution is instilled in a solution of 1.56 g of trans-(1RS)-1-formyl-(2RS)-2-[(1E, 3E)-(5R or 5S)-5-acetoxy-1,3-tridecadienyl-cycloheptane (diastereomer A) from example 9a) in 3 ml of tetrahydrofuran at −70° C. under argon and allowed to heat to −30° C. and stirred for 1 hour at this temperature. The reaction mixture is added to 100 ml of saturated aqueous ammoniumchloride solution and extracted three times with 100 ml of ethyl acetate each. The combined organic phases are washed once with semiconcentrated aqueous sodium chloride solution, dried on anhydrous sodium sulfate and after filtration concentrated by evaporation in a vacuum. The thus obtained residue is purified by multiple chromatography on silica gel. With hexane/ethyl acetate (85+15), 1.52 g of the alcohol is obtained as colorless oil.

IR (CHCl$_3$): 3610, 3460 (broad), 3005, 2930, 2860, 1724, 1467, 1378, 1255, 1100, 994, 840 cm$^{-1}$.

For acetylation 2.16 ml of acetic anhydride is added to a solution of 1.51 g of the above-described alcohol in 4.32 ml of pyridine and stirred for 18 hours at 0° C. Then it is diluted with 1 ml of water and concentrated by evaporation in a vacuum with addition of toluene. The thus obtained residue is purified by chromatography on silica gel. With hexane/0–10% ethyl acetate, 1.23 g of the acetate is obtained as colorless oil.

IR(CHCl$_3$): 3007, 2938, 2862, 1727, 1468, 1378, 1256, 1100, 993, 842 cm$^{-1}$.

For silylether cleavage 1.23 g of the above-produced acetate in 8.3 ml of tetrahydrofuran is stirred with 1.30 g of tetrabutylammonium fluoride trihydrate at 24° C. under argon for 3 hours. Then it is diluted with 70 ml of diethyl ether, washed three times with 20 ml of water each, once with saturated aqueous sodium chloride solution, dried on anhydrous sodium sulfate and after filtration concentrated by evaporation in a vacuum. The thus obtained residue is purified by chromatography on silica gel. With hexane/ 0–30% ethyl acetate, 895 mg of the title compound is obtained as colorless oil.

IR (CHCl$_3$): 3625, 3460 (broad), 3005, 2930, 2860, 1725, 1460, 1375, 1255, 992 cm$^{-1}$.

The initial material for the above title compound is produced as follows:

28a) trans-(1RS)-1-Formyl-(2RS)-2-[(1E,3E)-(5R or 5S)-5-acetoxy-1,3-tridecadienyl-cycloheptane (diastereomer A)

Analogously to example 20e) 1.56 g of the title compound is obtained from 1.61 g of (5R or 5S)-5-acetoxy-1-[trans-1-hydroxymethyl-cyclohept-2-yl]-(1E,3E)-trideca-1,3-diene (diastereomer A, 1st fraction from example 1d)), that is used without further purification.

IR (CHCl$_5$): 3020, 2928, 2858, 2720, 1722, 1460, 1373, 1247, 990 cm$^{-1}$.

EXAMPLE 29

(±)-(5RS)-5-Acetoxy-5-[trans-(2RS)-2-((1E,3E)-(5S or 5R)-5-acetoxy-1,3-tridecadienyl)-(1RS)-cycloheptyl]-pentan-1-ol (diastereomer B A solution of 2.48 g of 4-chloro-1-(tert.-butyldimethylsilyloxy)-butane in 2.1 ml of tetrahydrofuran is instilled in 541 mg of magnesium at 24° C. under argon, a crystal of iodine is added, heated for 10 minutes to 70° C., stirred for 30 minutes at 24° C. and diluted with 7.0 ml of tetrahydrofuran.

The above-produced Grignard solution is instilled in a solution of 1.31 g of trans-(1RS)-1-formyl-(2RS)-2-[(1E,3E)-(5S or 5R)-5-acetoxy-1,3-tridecadienyl-cycloheptane (diastereomer B) from example 10a) in 2.5 ml of tetrahydrofuran at –70° C. under argon and allowed to heat to –30° C. and stirred for 1 hour at this temperature. The reaction mixture is added to 100 ml of saturated aqueous ammoniumchloride solution and extracted three times with 100 ml of ethyl acetate each. The combined organic phases are washed once with semiconcentrated aqueous sodium chloride solution, dried on anhydrous sodium sulfate and after filtration concentrated by evaporation in a vacuum. The thus obtained residue is purified by multiple flash-chromatography on silica gel. With hexane/methyl-tert.-butylether (92+8), 726 mg of the alcohol is obtained as colorless oil.

IR (CHCl$_3$): 3610, 3450 (broad), 3005, 2930, 2860, 1725, 1465, 1375, 1253, 1098, 992, 838 cm$^{-1}$.

For acetylation 1 ml of acetic anhydride is added to a solution of 718 mg of the above-described alcohol in 2 ml of pyridine and stirred for 18 hours at 0° C. Then it is diluted with 0.5 ml of water and concentrated by evaporation in a vacuum with addition of toluene. The thus obtained residue is purified by chromatography on silica gel. With hexane/ 0–10% ethyl acetate, 687 mg of the acetate is obtained as colorless oil.

IR(CHCl$_3$): 3005, 2930, 2860, 1726, 1466, 1374, 1253, 1098, 992, 838 cm$^{-1}$.

For silylether cleavage 679 mg of the above-produced acetate in 4.6 ml of tetrahydrofuran is stirred with 723 mg of tetrabutylammonium fluoride trihydrate at 24° C. under argon for 3 hours. Then it is diluted with 50 ml of diethyl ether, washed three times with 10 ml of water each, once with saturated aqueous sodium chloride solution, dried on anhydrous sodium sulfate and after filtration concentrated by evaporation in a vacuum. The thus obtained residue is purified by chromatography on silica gel. With hexane/ 0–40% ethyl acetate, 552 mg of the title compound is obtained as colorless oil.

IR (CHCl$_3$): 3620, 3460 (broad), 3005, 2930, 2860, 1723, 1465, 1375, 1250, 992 cm$^{-1}$.

The initial material for the above title compound is produced as follows:

29a) trans-(1RS)-1-Formyl-(2RS)-2-[(1E,3E)-(5S or 5R)-5-acetoxy-1,3-tridecadienyl-cycloheptane (diastereomer B)

Analogously to example 20e) 1.31 g of the title compound is obtained from 1.36 g of (5S or 5R)-5-acetoxy-1-[trans-1-hydroxymethyl-cyclohept-2-yl]-(1E,3E)-trideca-1,3-diene (diastereomer B, 3rd fraction from example 1d)), that is used without further purification.

IR (CHCl$_3$): 3020, 2930, 2858, 2720, 1723, 1460, 1372, 1250, 990 cm$^{-1}$.

EXAMPLE 30

(±)-(5RS)-5-Acetoxy-5-[trans-(2RS)-2-((1E,3E)-(5R or 5S)-5-acetoxy-1,3-tridecadienyl-(1RS)-cycloheptyl]-pentanoic acid (diastereomer B)

For oxidation 891 of the title compound produced in example 28) is dissolved in 45 ml of dichloromethane, mixed with 7.51 g of Collins reagent at 0° C. under argon and stirred for 1 hour at 0° C. Then it is diluted with diethyl ether, mixed with Celite, filtered off on Celite and washed well with diethyl ether. The 1-aldehyde obtained after concentration by evaporation is immediately dissolved in 51 ml of acetone without further purification, mixed with 1.3 ml of Jones reagent (J. Chem. Soc. 1953, 2555) at 30° C. under argon and stirred for 20 minutes at this temperature. Then 0.5 ml of 2-propanol is added, stirred for 10 minutes, diluted with 100 ml of ethyl acetate, shaken four times with 30 ml of saturated aqueous sodium chloride solution each, dried on anhydrous sodium sulfate and after filtration concentrated by evaporation in a vacuum. The thus obtained residue is purified by chromatography on silica gel. With hexane/ 0–50% ethyl acetate, 483 mg of the title compound is obtained as colorless oil.

IR (film): 3450, 3200 (broad), 3020, 2930, 2858, 1738, 1710, 1458, 1372, 1242, 990 cm$^{-1}$.

EXAMPLE 31

(±)-(5RS)-5-Acetoxy-5-[trans-(2RS)-2-((1E,3E)-(5S or 5R)-5-acetoxy-1,3-tridecadienyl)-(1RS)-cycloheptyl]-pentanoic acid (diastereomer B)

For oxidation 541 mg of the title compound produced in example 29) is dissolved in 27 ml of dichloromethane, mixed with 4.57 g of Collins reagent at 0° C. under argon and stirred for 1 hour at 0° C. Then it is diluted with diethyl ether, mixed with Celite, filtered off on Celite and washed well with diethyl ether. The 1-aldehyde obtained after concentration by evaporation is immediately dissolved in 30 ml of acetone without further purification, mixed with 0.75 ml of Jones reagent at 30° C. under argon and stirred for 20 minutes at this temperature. Then 0.3 ml of 2-propanol is added, stirred for 10 minutes, diluted with 100 ml of ethyl acetate, shaken four times with 30 ml of semiconcentrated aqueous sodium chloride solution each, dried on anhydrous sodium sulfate and after filtration concentrated by evaporation in a vacuum. The thus obtained residue is purified by chromatography on silica gel. With hexane/0–40% ethyl acetate, 326 mg of the title compound is obtained as colorless oil.

IR (CHCl$_3$): 3450, 3200 (broad), 3020, 2928, 2858, 1738, 1710, 1460, 1372, 1240, 992 cm$^{-1}$.

EXAMPLE 32

(±)-(5RS)-5-Acetoxy-5-[trans-(2RS)-2-((1E,3E)-(5R or 5S)-5-hydroxy-1,3-tridecadienyl)-(1RS)-cycloheptyl]-pentanoic acid (diastereomer A)

Analogously to example 21), 121 mg of the title compound is obtained as colorless oil from 150 mg of (±)-(5RS)-5-acetoxy-5-[trans-(2RS)-2-((1E,3E)-(5R or 5S)-5-acetoxy-1,3-tridecadienyl)-(1RS)-cycloheptyl]-pentanoic acid (diastereomer A) from example 11).

IR (film): 3440, 3200 (broad), 3020, 2928, 2857, 1737, 1712, 1458, 1375, 1242, 990 cm$^{-1}$.

EXAMPLE 33

(±)-(5RS)-5-Acetoxy-5-[trans-(2RS)-2-((1E,3E)-(5S or 5R)-5-hydroxy-1,3-tridecadienyl)-(1RS)-cycloheptyl]-pentanoic acid (diastereomer B)

Analogously to example 21), 89.8 mg of the title compound is obtained as colorless oil from 125 mg of (±)-(5RS)-5-acetoxy-5-[trans-(2RS)-2-((1E,3E)-(5S or 5R)-5-acetoxy-1,3-tridecadienyl)-(1RS)-cycloheptyl]-pentanoic acid (diastereomer B) from example 12).

IR (film): 3440, 3100 (broad), 3020, 2925, 2860, 1730, 1705, 1467, 1375, 1260, 988 cm$^{-1}$.

EXAMPLE 34

(±)-(5RS)-5-Hydroxy-5-[trans-(2RS)-2-((1E,3E)-(5R or 5S)-5-hydroxy-1,3-tridecadienyl)-(1RS)-cycloheptyl]-pentanoic acid (diastereomer A) and (±)-(5RS)-5-hydroxy-5-[trans-[2RS)-2-((1E, 3E)-(5R or 5S)-5-hydroxy-1,3-tridecadienyl)-(1RS)-cycloheptyl ]-pentanoic acid-1,5-lactone (diastereomer A)

Analogously to example 22, 40.1 mg of (±)-(5RS)-5-hydroxy-5-[trans-(2RS)-2-((1E,3E)-(5R or 5S)-5-hydroxy-1,3-tridecadienyl-(1RS)-cycloheptyl]-pentanoic acid-1,5-lactone (diastereomer A) in a more nonpolar fraction and 8.8 mg of (±)-(5RS)-5-hydroxy-5-[trans-(2RS)-2-((1E,3E)-(5R or 5S)-5-hydroxy-1,3-tridecadienyl-(1RS)-cycloheptyl]-pentanoic acid (diastereomer A) in a more polar fraction are obtained as colorless oils from 170 mg of (±)-(5RS)-5-acetoxy-5-[trans-(2RS)-2-((1E,3E)-(5R or 5S)-5 -acetoxy-1, 3-tridecadienyl)-(1RS)-cycloheptyl]-pentanoic acid (diastereomer A) from example 11).

IR (film; lactone): 3440, 3018, 2930, 2855, 1733, 1465, 1245, 900 cm$^{-1}$.

IR (film; acid): 3435 (broad), 3200 (broad), 3020, 2925, 2855, 1725, 1463, 1308, 992 cm$^{-1}$.

EXAMPLE 35

(±)-(5RS)-5-Hydroxy-5-[trans-(2RS)-2-((1E,3E)-(5S or 5R)-5-hydroxy-1,3-tridecadienyl)-(1RS)-cycloheptyl]-pentanoic acid (diastereomer B) and (±)-(5RS)-5-hydroxy-5-[trans- (2RS)-2-((1E, 3E)-(5S or 5R)-5-hydroxy-1,3-tridecadienyl)-(1RS)-cycloheptyl] -pentanoic acid-1,5-lactone (diastereomer B)

Analogously to example 22, 29 mg of (±)-(5RS)-5-hydroxy-5-[trans-(2RS)-2-((1E,3E)-(5S or 5R)-5-hydroxy-1,3-tridecadienyl-(1RS)-cycloheptyl]-pentanoic acid-1,5-lactone (diastereomer B) in a more nonpolar fraction and 17.9 mg of (±)-(5RS)-5-hydroxy-5-[trans-(2RS)-2-((1E,3E)-(5S or 5R)-5-hydroxy-1,3-tridecadienyl-(1RS)-cycloheptyl]-pentanoic acid (diastereomer B) in a more polar fraction are obtained as colorless oils from 125 mg of (±)-(5RS)-5-acetoxy-5-[trans-(2RS)-2-((1E,3E)-(5S or 5R)-5 -acetoxy-1, 3-tridecadienyl)-(1RS)-cycloheptyl]-pentanoic acid (diastereomer B) from example 12).

IR (film; lactone): 3440 (broad), 3020, 2925, 2858, 1732, 1464, 1245, 990 cm$^{-1}$.

IR (film; acid): 3415 (broad), 3015, 2924, 2857, 1713, 1462, 1378, 1250, 990 cm$^{-1}$.

EXAMPLE 36

(±)-(5RS)-5-Acetoxy-5-[trans-(2RS)-2-((1E,3E)-(5R or 5S)-5-acetoxy-1,3-tridecadienyl)-(1RS)-cycloheptyl]-pentanoic acid methyl ester (diastereomer A)

An ethereal diazomethane solution is instilled until permanent yellow coloring in a solution of 43 mg (±)-(5RS)-5-acetoxy- 5-[trans-(2RS)-2-((1E,3E)-(5R or 5S)-5-acetoxy-1,3 -tridecadienyl)-(1RS)-cycloheptyl]-pentanoic acid (diastereomer A) from example 30 in 4 ml of dichloromethane at 0° C. under argon, stirred for 15 minutes at 0° C. and then concentrated by evaporation in a vacuum. The thus obtained residue is purified by chromatography on silica gel. With hexane/0–10% ethyl acetate, 36 mg of the title compound is obtained as colorless oil.

IR (CHCl$_3$): 3005, 2935, 2860, 1730, 1460, 1376, 1255, 990 cm$^{-1}$.

EXAMPLE 37

(±)-(5RS)-5-Acetoxy-5-[trans-(2RS)-2-((1E,3E)-(5S or 5R)-5-hydroxy-1,3-tridecadienyl)-(1RS)-cycloheptyl]-pentanoic acid-tris(hydroxymethyl)-amino methane salt (diastereomer B)

A solution of 4 mg of tris-(hydroxymethyl)-aminomethane in 0.02 ml of water is added at 70° C. to a solution of 10 mg of (±)-(5RS)-5-hydroxy-5-[trans-(2RS)-2-((1E,3E)-(5S or 5R)-5 -hydroxy-1,3-tridecadienyl-(1RS)-cycloheptyl]-pentanoic acid (diastereomer B) from example 16) in 1.5 ml of acetonitrile. It is allowed to cool with stirring, decanted after 16 hours from the solvent and the residue is dried in a vacuum. 3.3 mg of the title compound is isolated as waxy material.

We claim:

1. A leukotriene-B$_4$ compound of formula I in which

R$^1$ means CH$_2$OH, CH$_3$, CF$_3$, COOR$^5$, CONR$^6$R$^7$, or

R$^1$ together with R$^2$ means a carbonyl group,

R² and R³ are the same or different and represent H or an organic acid radical with 1–15 C atoms, R⁴ symbolizes H, ($C_1$–$C_{10}$) alkyl optionally substituted once or several times by chlorine or bromine, $C_3$–$C_{10}$ cycloalkyl, $C_6$–$C_{10}$ aryl radical optionally substituted, independent from one another, once or several times by chlorine, bromine, phenyl, $C_1$–$C_4$ alkyl, $C_1$–$C_4$ alkoxy, fluoromethyl, chloromethyl, trifluoromethyl, carboxy or hydroxy, or a 5- or 6-membered aromatic heterocyclic ring with at least 1 heteroatom, R⁵ means hydrogen, $C_1$–$C_{10}$ alkyl, $C_3$–$C_{10}$ cycloalkyl, $C_6$–$C_{10}$ aryl radical optionally substituted by 1–3 chlorine, bromine, phenyl, $C_1$–$C_4$ alkyl, $C_1$–$C_4$ alkoxy, fluoromethyl, chloromethyl, trifluoromethyl, carboxy or hydroxy, $CH_2$—CO—($C_6$–$C_{10}$) aryl or a 5- or 6-membered ring with at least 1 heteroatom, A symbolizes a trans, trans-CH=CH—CH=CH, a —$CH_2CH_2$—CH=CH— or a tetramethylene group, B symbolizes a $C_1$–$C_{10}$ straight-chain or branched-chain alkylene group, which optionally can be substituted by fluorine or the group

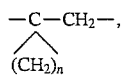

D can mean a direct bond, oxygen, sulfur, —C≡C—, —CH=CR⁸ or together with

B can also mean a direct bond,

R⁶ and R⁷ are the same or different and represent H or $C_1$–$C_4$ alkyl or R⁷ represents H and R⁶ represents $C_1$–$C_{10}$ alkanoyl or $C_1$–$C_{10}$ alkanesulfonyl, R⁸ means H, $C_1$–$C_{15}$ alkyl, chlorine, bromine, and n is 3–5 as well as, if R⁵ means hydrogen, their salts with physiologically compatible bases and their cyclodextrin clathrates.

2. A compound according to claim 1, which is (±)-(5RS)-5-Acetoxy-5-[cis-(2RS)-2-((1E,3E)-(5RS)-5-acetoxy-1,3-tridecadienyl)-(1RS)-cyclobutyl]-pentan-1-ol.

3. A compound according to claim 1, which is (±)-(5RS)-5-Acetoxy-5-[cis-(2RS)-2-((1E,3E)-(5RS)-5-acetoxy-1,3-tridecadienyl)-(1RS)-cyclobutyl]-pentanoic acid.

4. A compound according to claim 1, which is (±)-(5RS)-5-Acetoxy-5-[cis-(2RS)-2-((1E,3E)-(5RS)-5-hydroxy-1,3-tridecadienyl)-(1RS)-cyclobutyl]-pentanoic acid.

5. A compound according to claim 1, which is (±)-(5RS)-5-Hydroxy-5-[cis-(2RS)-2-((1E,3E)-(5RS)-5-hydroxy-1,3-tridecadienyl)-(1RS)-cyclobutyl]-pentan-1-ol.

6. A compound according to claim 1, which is (±)-(5RS)-5-Acetoxy-5-[trans-(2RS)-2-((1E,3E)-(5RS)-5-acetoxy-1,3-tridecadienyl)-(1RS)-cyclobutyl]-pentanoic acid.

7. A compound according to claim 1, which is (±)-(5RS)-5-Acetoxy-5-[trans-(2RS)-2-((1E,3E)-(5RS)-5-acetoxy-1,3-tridecadienyl)-(1RS)-cyclobutyl]-pentan-1-ol.

8. A compound according to claim 1, which is (±)-(5RS)-5-Hydroxy-5-[trans-(2RS)-2-((1E,3E)-(5RS)-5-hydroxy-1,3-tridecadienyl)-(1RS)-cyclobutyl]-pentanoic acid.

9. A compound according to claim 1, which is (±)-(5RS)-5-Acetoxy-5-[trans-(2RS)-2-((1E,3E)-(5RS)-5-hydroxy-1,3-tridecadienyl)-(1RS)-cyclobutyl]-pentanoic acid.

10. A compound according to claim 1, which is (±)-(5RS)-5-Hydroxy-5-[cis-(2RS)-2-((1E,3E)-(5RS)-5-hydroxy-1,3-tridecadienyl)-(1RS)-cyclobutyl]-pentanoic acid methyl ester.

11. A compound according to claim 1, which is (±)-(5RS)-5-Acetoxy-5-[cis-(2RS)-2-((1E,3E)-(5RS)-5-hydroxy-1,3-tridecadienyl)-(1RS)-cyclobutyl]-pentanoic acid methyl ester.

12. A compound according to claim 1, which is (±)-(5RS)-5-Hydroxy-5-[cis-(2RS)-2-((1E,3E)-(5RS)-5-hydroxy-1,3-tridecadienyl)-(1RS)-cyclobutyl]-pentanoic acid-tris(hydroxymethyl)-aminomethane salt.

13. A compound according to claim 1, which is (±)-(5RS)-3-[cis-(2RS)-2-((1E,3E)-(5RS)-5-hydroxy-1,3-tridecadienyl)-(1RS)-cyclobutyl]-pentanolactone.

14. A compound according to claim 1, which is (±)-(5RS)-5-Acetoxy-5-[cis-(2RS)-2-((1E,3E)-(5RS)-5-acetoxy-1,3-tridecadienyl)-(1RS)-cyclobutyl]-pentan-1-ol.

15. A compound according to claim 1, which is (±)-(5RS)-5-Acetoxy-5-[cis-(2RS)-2-((1E,3E)-(5RS)-5-acetoxy-1,3-tridecadienyl)-(1RS)-cyclobutyl]-pentanoic acid.

16. A compound according to claim 1, which is (±)-(5RS)-5-Acetoxy-5-[cis-(2RS)-2-((1E,3E)-(5RS)-5-hydroxy-1,3-tridecadienyl-(1RS)-cyclobutyl]-pentanoic acid.

17. A compound according to claim 1, which is (±)-(5RS)-5-Hydroxy-5-[cis-(2RS)-2-((1E,3E)-(5RS)-5-hydroxy-1,3-tridecadienyl)-(1RS)-cyclobutyl]-pentan-1-ol.

18. A pharmaceutical composition comprising a compound according to claim 1 and a pharmaceutically-acceptable carrier.

19. A process for the production of a leukotriene-$B_4$ compound of formula I according to claim 1, wherein an aldehyde of formula II

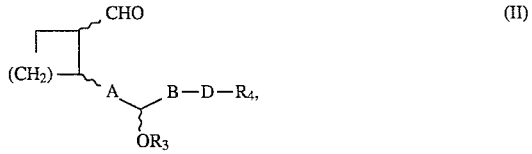

in which A, B, D, R³ and R⁴ have the above-indicated meanings, optionally after protection of free hydroxy groups with a magnesium-organic compound of formula III,

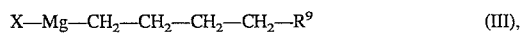

in which X represents chlorine, bromime or iodine and R⁹ represents —$CH_3$, $CF_3$ or $OR^{10}$, in which $R_{10}$ means an easily cleavable ether radical, is reacted and optionally then isomers are separated in any sequence, protected hydroxy groups are released and/or a free hydroxy group is esterified and/or the 1-hydroxy group is oxidized to carboxylic acid and/or double bonds are hydrogenated and/or an esterified carboxyl group (R¹=COOR⁵) is saponified and/or reduced and/or a carboxyl group (R⁵=H) is converted to an amide (R¹=CONHR⁶R⁷) or a carboxyl group with a physiologically compatible base is converted to a salt.

20. A method for treating a patient comprising administering a compound of claim 1.

* * * * *